US011897828B1

(12) United States Patent
Lindberg et al.

(10) Patent No.: US 11,897,828 B1
(45) Date of Patent: *Feb. 13, 2024

(54) THERMOCHEMICAL REACTIONS USING GEOTHERMAL ENERGY

(71) Applicant: EnhancedGEO Holdings, LLC, St. Petersburg, FL (US)

(72) Inventors: Greg Lindberg, Thonotosassa, FL (US); Kimberly C. Conner, Wetumpka, AL (US)

(73) Assignee: EnhancedGEO, Holdings, LLC, St. Petersburg, FL (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/117,313

(22) Filed: Mar. 3, 2023

(51) Int. Cl.
| | | |
|---|---|---|
| *C07C 1/12* | (2006.01) | |
| *C01B 3/04* | (2006.01) | |
| *B01J 12/00* | (2006.01) | |
| *B01J 19/24* | (2006.01) | |
| *B01J 23/89* | (2006.01) | |
| *E21B 41/00* | (2006.01) | |
| *F24T 10/10* | (2018.01) | |

(Continued)

(52) U.S. Cl.
CPC ............... *C07C 1/12* (2013.01); *B01J 12/005* (2013.01); *B01J 12/007* (2013.01); *B01J 19/2465* (2013.01); *B01J 21/04* (2013.01); *B01J 23/892* (2013.01); *C01B 3/045* (2013.01); *E21B 41/00* (2013.01); *F24T 10/10* (2018.05); *F24T 10/30* (2018.05); *B01J 2219/00103* (2013.01); *C07C 2521/04* (2013.01); *C07C 2523/89* (2013.01)

(58) Field of Classification Search
CPC ....... C01C 1/12; E21B 41/00; C07C 2523/89; C07C 2521/04; B01J 12/005; B01J 12/007; B01J 19/2465
See application file for complete search history.

(56) References Cited

U.S. PATENT DOCUMENTS

| | | |
|---|---|---|
| 3,498,381 A | 3/1970 | Earlougher, Jr. |
| 3,757,516 A | 9/1973 | Mc |

(Continued)

FOREIGN PATENT DOCUMENTS

| | | |
|---|---|---|
| AU | 2018308861 A1 | 1/2020 |
| AU | 2017268378 B2 | 9/2021 |

(Continued)

OTHER PUBLICATIONS

Boehm, R.F. et al., Modelling of a Magma Energy Geothermal Power Plant, presented at ASME Winter Annual Meeting, Boston MA, Dec. 1987, SAND-87-0564C, DE88 003793, 11 pages.

(Continued)

*Primary Examiner* — Jafar F Parsa
(74) *Attorney, Agent, or Firm* — Stephen Y. Liu; Carstens, Allen & Gourley, LLP

(57) ABSTRACT

A reaction system includes a wellbore extending from a surface into a subterranean heat source. The reaction system further includes a reaction chamber configured to be maintained at a reaction temperature using heat from the subterranean heat source. The reaction system further includes one or more inlet conduits. The inlet conduits are configured to provide one or more feed streams to the reaction chamber. The reaction system also includes outlet conduits configured to allow flow of one or more product streams.

7 Claims, 12 Drawing Sheets

(51) Int. Cl.
*F24T 10/30* (2018.01)
*B01J 21/04* (2006.01)

(56) References Cited

U.S. PATENT DOCUMENTS

| | | | |
|---|---|---|---|
| 3,864,208 | A | 2/1975 | Van |
| 3,950,949 | A | 4/1976 | Martin et al. |
| 3,957,108 | A | 5/1976 | Huisen |
| 4,043,129 | A | 8/1977 | McCabe et al. |
| 4,054,176 | A | 10/1977 | Huisen |
| 4,140,184 | A | 2/1979 | Bechtold et al. |
| 4,665,705 | A | 5/1987 | Bonham, Jr. |
| 4,929,348 | A | 5/1990 | Rice |
| 5,860,279 | A | 1/1999 | Bronicki et al. |
| 5,911,684 | A | 6/1999 | Shnell |
| 7,124,584 | B1 | 10/2006 | Wetzel et al. |
| 8,047,285 | B1 | 11/2011 | Smith |
| 8,524,787 | B2 | 9/2013 | Ermolaev et al. |
| 9,006,298 | B2 | 4/2015 | Leviness et al. |
| 9,108,858 | B2 | 8/2015 | McDonald et al. |
| 9,150,423 | B2 | 10/2015 | Hosono et al. |
| 9,182,149 | B2 | 11/2015 | Gilaberte et al. |
| 9,298,756 | B1 | 3/2016 | Johnson |
| 9,359,271 | B2 | 6/2016 | Leviness et al. |
| 9,388,797 | B2 | 7/2016 | Bronicki |
| 9,738,835 | B2 | 8/2017 | Schrauwen |
| 9,765,605 | B2 | 9/2017 | Williamson et al. |
| 10,017,395 | B2 | 7/2018 | Kageyama et al. |
| 10,058,848 | B2 | 8/2018 | Lipiec et al. |
| 10,131,545 | B2 | 11/2018 | Sekine et al. |
| 10,173,202 | B2 | 1/2019 | Hosono et al. |
| 10,322,940 | B2 | 6/2019 | Hosono et al. |
| 10,344,233 | B2 | 7/2019 | Lucas et al. |
| 10,358,604 | B2 | 7/2019 | Harris et al. |
| 10,710,049 | B2 | 7/2020 | Mikhajlov et al. |
| 10,745,625 | B2 | 8/2020 | Dogterom et al. |
| 10,759,668 | B2 | 9/2020 | Hosono et al. |
| 10,792,645 | B2 | 10/2020 | Hosono et al. |
| 10,974,969 | B2 | 4/2021 | Hu et al. |
| 11,131,484 | B2 | 9/2021 | McBay |
| 11,235,310 | B2 | 2/2022 | Hosono et al. |
| 11,286,169 | B2 | 3/2022 | Beach et al. |
| 11,325,105 | B2 | 5/2022 | Beach et al. |
| 2004/0265158 | A1 | 12/2004 | Boyapati et al. |
| 2006/0026961 | A1 | 2/2006 | Bronicki |
| 2006/0180537 | A1 | 8/2006 | Loftis et al. |
| 2006/0277917 | A1 | 12/2006 | Hsu |
| 2008/0213157 | A1 | 9/2008 | McGrady et al. |
| 2010/0025260 | A1 | 2/2010 | Naterer et al. |
| 2010/0045042 | A1 | 2/2010 | Hinders et al. |
| 2013/0101492 | A1* | 4/2013 | McAlister ............. C01B 3/24 422/162 |
| 2013/0232973 | A1 | 9/2013 | McBay |
| 2013/0234444 | A1 | 9/2013 | Rogers et al. |
| 2013/0333383 | A1 | 12/2013 | Schwarck |
| 2014/0262137 | A1 | 9/2014 | McBay |
| 2015/0128931 | A1 | 5/2015 | Joshi et al. |
| 2015/0300327 | A1 | 10/2015 | Sweatman et al. |
| 2015/0368565 | A1 | 12/2015 | Schrauwen |
| 2015/0377211 | A1 | 12/2015 | Occhiello |
| 2016/0097376 | A1 | 4/2016 | Wasyluk et al. |
| 2016/0115945 | A1 | 4/2016 | Barsi et al. |
| 2016/0363350 | A1 | 12/2016 | Tahara |
| 2017/0253492 | A1 | 9/2017 | Beach et al. |
| 2018/0106138 | A1 | 4/2018 | Randolph |
| 2018/0224164 | A1 | 8/2018 | Lakic |
| 2020/0040267 | A1 | 2/2020 | Willigenburg et al. |
| 2020/0231455 | A1 | 7/2020 | Beach et al. |
| 2020/0325030 | A1 | 10/2020 | Cussler et al. |
| 2020/0353518 | A1 | 11/2020 | Chandran et al. |
| 2021/0114005 | A1 | 4/2021 | Tao et al. |
| 2021/0122656 | A1 | 4/2021 | Willberg et al. |
| 2023/0130169 | A1 | 4/2023 | McIntyre |

FOREIGN PATENT DOCUMENTS

| | | |
|---|---|---|
| AU | 2016398360 B2 | 1/2022 |
| CN | 105148824 A | 12/2015 |
| CN | 108952650 A | 12/2018 |
| CN | 112604697 A | 4/2021 |
| CN | 113494273 A | 10/2021 |
| CN | 113562692 A | 10/2021 |
| EP | 0236640 A1 | 9/1987 |
| EP | 2792010 B1 | 1/2018 |
| EP | 3583321 A1 | 12/2019 |
| GB | 2592695 A | 9/2021 |
| GB | 2615913 A | 8/2023 |
| JP | h07286760 A | 10/1995 |
| JP | 2011052621 A | 3/2011 |
| JP | 2014202149 A | 10/2014 |
| JP | 2020067027 A | 4/2020 |
| WO | 2012079078 A2 | 6/2012 |
| WO | 2012037571 A3 | 7/2012 |
| WO | 2013025640 A2 | 2/2013 |
| WO | 2016204287 A1 | 12/2016 |
| WO | 2020150245 A1 | 7/2020 |
| WO | 2020160500 A1 | 8/2020 |
| WO | 2021257944 A9 | 4/2022 |
| WO | 2022123626 A1 | 6/2022 |
| WO | WO-2022211643 A1 * | 10/2022 ............. E21B 43/00 |

OTHER PUBLICATIONS

Colp, John L., Final Report—Magma Energy Research Project, Sandia Report, Sand82-2377, Unlimited Release, UC-66, prepared by Sandia National Laboratories under contrace DE-AC04-76DP00789, Printed Oct. 1982, 42 pages.

* cited by examiner

THERMOCHEMICAL REACTIONS USING GEOTHERMAL ENERGY

TECHNICAL FIELD

The present disclosure relates generally to systems and related methods for carrying out thermochemical processes, and more particularly to thermochemical reactions using geothermal energy.

BACKGROUND

Solar power and wind power are commonly available sources of renewable energy, but both are notoriously unreliable and have relatively poor power densities. In contrast, geothermal energy has high power density and is capable of operating despite weather conditions or time of day. However, the lack of necessary technological advances renders geothermal energy an impractical substitute.

Thermochemical reactions can be carried out to create useful end products such as hydrogen, ammonia, methane, diesel, kerosene, gasoline, and other forms of green fuel. Thermochemical reactions can only be carried out at elevated temperatures that provide the requisite activation energy. Some of these chemical reactions can be carried out at room temperature, but only economically at elevated temperatures that provides a desired rate of reaction. However, the costs associated with obtaining the elevated temperatures may render these processes impractical.

SUMMARY

Most existing geothermal energy systems are used for heating applications, such as to heat a home or other space. Where geothermal has been attempted for energy production or other higher temperature applications, previous geothermal systems have required significant expenditure of finances, labor, and equipment, rendering them impractical for commercial development. Most previous geothermal systems tap into low temperature resources of less than 194° F. that are relatively near the surface, significantly limiting applications and locations where previous geothermal systems can be deployed. In addition to other disadvantages of previous geothermal technology, the inability of previous technology to efficiently and reliably access high-temperature underground geothermal resources renders conventional geothermal systems technologically and financially impractical.

As used herein, "magma" refers to extremely hot liquid and semi-liquid rock under the Earth's surface. Magma is formed from molten or semi-molten rock mixture found typically between 1 km to 10 km under the surface of the Earth. As used herein, "lava" refers to molten or partially molten rock that has been expelled from the interior of the earth onto its surface. As used herein, "lava lake" is a large volume of molten lava. As used herein, "lava flow" is an outpouring of lava during an effusive eruption. As used herein, "lava tube" is a natural conduit formed by flowing lava from a volcanic vent that moves beneath the hardened surface of a lava flow. As used herein, "borehole" refers to a hole that is drilled to aid in the exploration and recovery of natural resources, including oil, gas, water, or heat from below the surface of the Earth. As used herein, a "wellbore" refers to a borehole either alone or in combination with one or more other components disposed within or in connection with the borehole in order to perform exploration and/or recovery processes.

The present disclosure is directed to a method for carrying out thermochemical processes. The method includes the steps of injecting one or more feed streams into a reaction chamber, maintaining the one or more feed streams in the reaction chamber for a residence time to form one or more product streams from the one or more feed streams, and removing the one or more product streams from the reaction chamber. The reaction chamber is maintained at a reaction temperature using heat obtained directly or indirectly from a subterranean heat source or a surface heat source. An example of a surface geothermal heat source is lava, lava flow, or body of lava such as a lava lake or a lava tube. An example of a subterranean heat source is a magma body, also referred to herein as a magma reservoir. For example, heat may be obtained indirectly from a subterranean heat source by facilitating heat transfer between reactants and a fluid (e.g., steam or superheated steam) heated by the subterranean heat source and/or directly by placing the reactant in close proximity to the subterranean heat source (e.g., in a reaction vessel placed within a wellbore extending into the subterranean heat source.

Aspects of the present disclosure are also directed to a system for carrying out thermochemical processes. The system includes a wellbore extending from a surface towards a subterranean heat source and a reaction chamber configured to be maintained at a reaction temperature using heat obtained directly or indirectly from the subterranean heat source. In some embodiments, the reaction chamber includes one or more inlets configured to receive one or more feed streams and one or more outlets configured to expel one or more product streams from the reaction chamber. The one or more product streams are formed from the one or more feed streams in response to maintaining the one or more feed streams within the reaction chamber for a residence time.

In certain embodiments, the present disclosure is directed to a method for carrying out thermochemical splitting of water. The method includes the steps of injecting one or more feed streams comprising water into a reaction chamber, maintaining the one or more feed streams in the reaction chamber for a residence time to form hydrogen and water product streams from the one or more feed streams, and removing the one or more product streams from the reaction chamber. The reaction chamber is maintained at a reaction temperature using heat obtained directly or indirectly from a subterranean heat source.

Aspects of the present disclosure are also directed to a system for carrying out thermochemical splitting of water. The system includes a wellbore extending from a surface towards a subterranean heat source and a reaction chamber configured to be maintained at a reaction temperature using heat obtained directly from the subterranean heat source. In some embodiments, the reaction chamber includes one or more inlets configured to receive one or more feed streams and one or more outlets configured to expel one or more product streams from the reaction chamber. The one or more product streams are formed from the one or more feed streams in response to maintaining the one or more feed streams within the reaction chamber for a residence time.

In certain embodiments, the present disclosure is directed to a method for producing hydrocarbons, including but not limited to gaseous or liquid hydrocarbons. The method includes the steps of injecting one or more feed streams comprising oxides of carbon, hydrogen, and/or water into a reaction chamber, maintaining the one or more feed streams in the reaction chamber for a residence time to form the desired hydrocarbon product streams from the one or more feed streams, and removing the one or more product streams from the reaction chamber. The reaction chamber is maintained at a reaction temperature using heat obtained directly or indirectly from a subterranean heat source.

Aspects of the present disclosure are also directed to a system for producing hydrocarbons. The system includes a wellbore extending from a surface towards a subterranean heat source and a reaction chamber configured to be maintained at a reaction temperature using heat obtained directly from the subterranean heat source. In some embodiments, the reaction chamber includes one or more inlets configured to receive one or more feed streams and one or more outlets configured to expel one or more product streams from the reaction chamber. The one or more product streams are formed from the one or more feed streams in response to maintaining the one or more feed streams within the reaction chamber for a residence time.

Other aspects, embodiments and features of the disclosure will become apparent from the following detailed description when considered in conjunction with the accompanying figures. In the figures, each identical, or substantially similar component that is illustrated in various figures is represented by a single numeral or notation. For purposes of clarity, not every component is labeled in every figure. Nor is every component of each embodiment shown where illustration is not necessary to allow those of ordinary skill in the art to understand the disclosure.

BRIEF DESCRIPTION OF THE FIGURES

For a more complete understanding of the present disclosure, reference is now made to the following description, taken in conjunction with the accompanying drawings and detailed description, in which like reference numerals represent like parts.

DETAILED DESCRIPTION

Embodiments of the present disclosure and its advantages will become apparent from the following detailed description when considered in conjunction with the accompanying figures. In the figures, each identical, or substantially similar component that is illustrated in various figures is represented by a single numeral or notation. For purposes of clarity, not every component is labeled in every figure, nor is every component of each embodiment shown where illustration is not necessary to allow those of ordinary skill in the art to understand the disclosure.

Previous geothermal power generation systems typically require significant expenditure of finances, manpower, and equipment. Most previous geothermal systems tap into low temperature resources of less than 194° F. that are relatively near the surface. The inability of previous technology to efficiently and reliably access high-temperature geothermal resources renders conventional geothermal systems technologically and financially impractical.

The present disclosure includes the unexpected observations including that (1) magma reservoirs can be located at relatively shallow depths of less than 2.5 km; (2) the top layer of a magma reservoir may have relatively few crystals with little or no mush zone; (3) rock near or around magma reservoirs is generally not ductile and can support fractures; (4) a magma reservoir does not decline in thermal output over at least a two-year period; (5) eruptions at drill sites into magma reservoirs are unlikely (e.g., eruptions have not happened at the African and Icelandic drill sites in over 10,000 years and it is believed the Kilauea, Hawaii drill site has never erupted); and (6) drilling into magma reservoirs is reasonably safe and rising magma can be quenched with water to form a rock plug.

This disclosure recognizes the need for a geothermal system that takes advantage of the unexpected observations described above by harnessing a geothermal resource with a sufficiently high temperature that can provide a sufficiently high temperature for desired processes. For example, an underground geothermal reservoir, such as a magma reservoir, may facilitate the generation of high-temperature, high-pressure steam, while avoiding problems associated with conventional systems.

Figure 1:
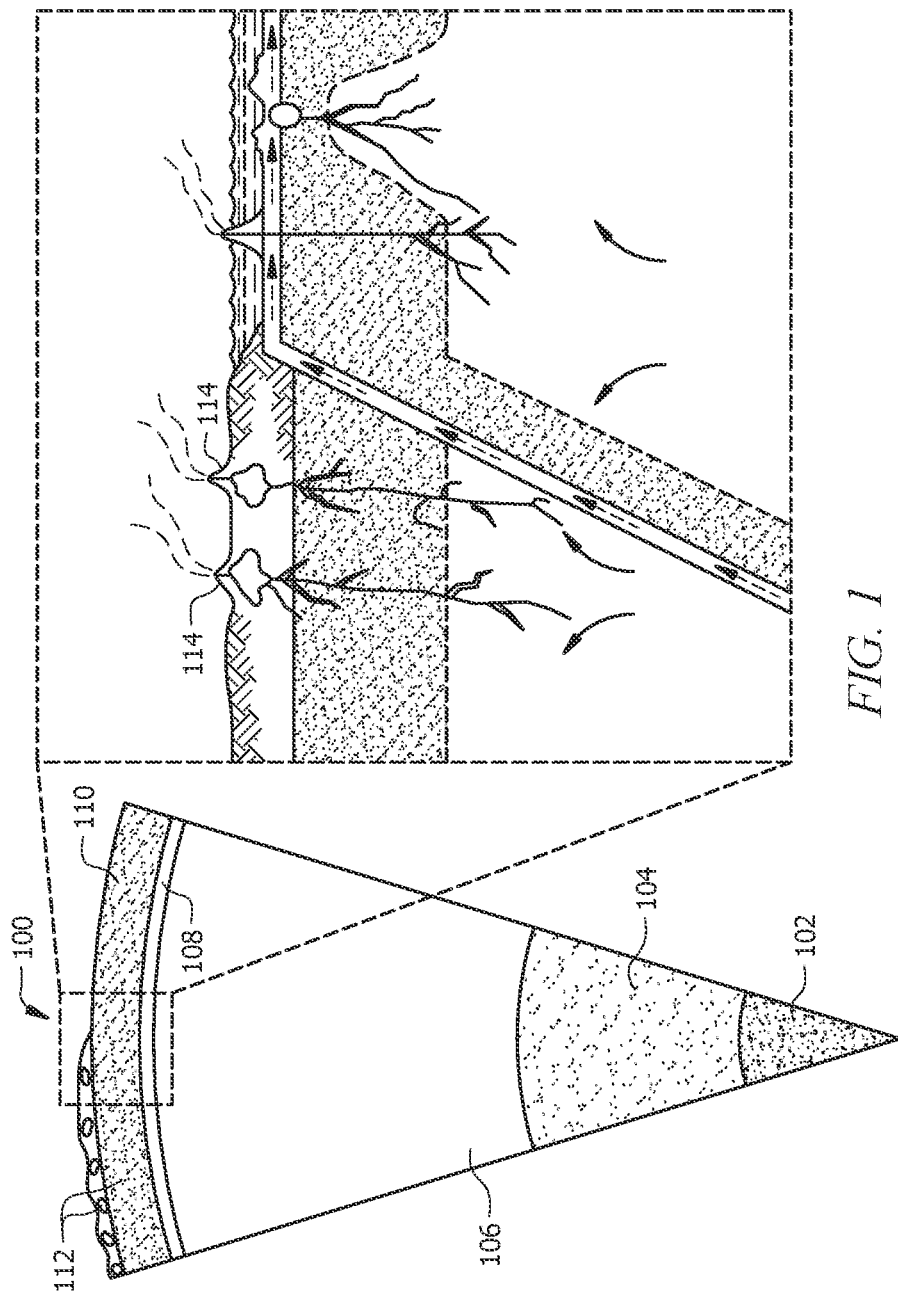
FIG. 1 is a diagram of underground regions in the Earth.

FIG. 1 is a partial cross-sectional diagram of the Earth 100 depicting underground formations that can be tapped by geothermal systems of this disclosure for conducting thermochemical reactions. The Earth 100 is composed of an inner core 102, outer core 104, lower mantle 106, transition zone 108, upper mantle 110, and crust 112. There are places on the Earth 100 where magma reaches the surface of the crust 112 forming volcanoes 114. However, in most cases, magma approaches only within a few miles or less from the surface. This magma can heat ground water to temperatures sufficient for certain geothermal power production. However, for other applications, such as geothermal energy production and to harness geothermal energy to carry out thermochemical reactions, more direct heat transfer with the magma is desirable.

Figure 2:
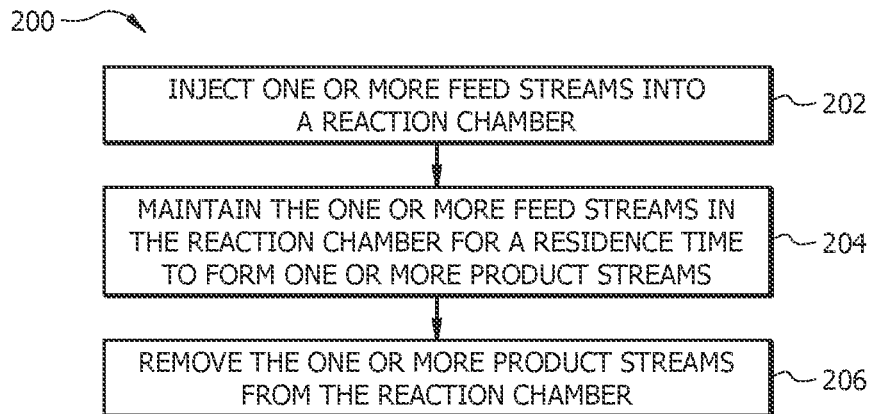
FIG. 2 is a flowchart of a process for carrying out a thermochemical process according to an illustrative embodiment.

FIG. 2 is a flowchart of a process for carrying out a thermochemical process according to an illustrative embodiment. The steps in flowchart 200 can be carried out in a system, such as systems 600a and 600b in FIGS. 6A and 6B, or in the various systems described in FIGS. 7-11.

Flowchart 200 begins at step 202 by injecting one or more feed streams into a reaction chamber, such as reaction chamber 612. The reaction chamber is maintained at a reaction temperature using heat obtained directly or indirectly from a subterranean heat source (e.g., a magma reservoir). An example of the subterranean heat source includes magma body 608.

In step 204, the one or more feed streams is maintained in the reaction chamber for a residence time to form one or more product streams from the one or more feed streams. The one or more product streams are removed from the reaction chamber in step 206. The one or more product streams can be an intermediate product stream, such as intermediate product stream 1110, which can be further processed to form one or more end product streams, such as end product stream 706, gas-phase end products 1118, and/or liquid-phase end products 1116. The one or more product streams can also be an end product stream that does not require further processing, such as product stream 606.

Figure 3:
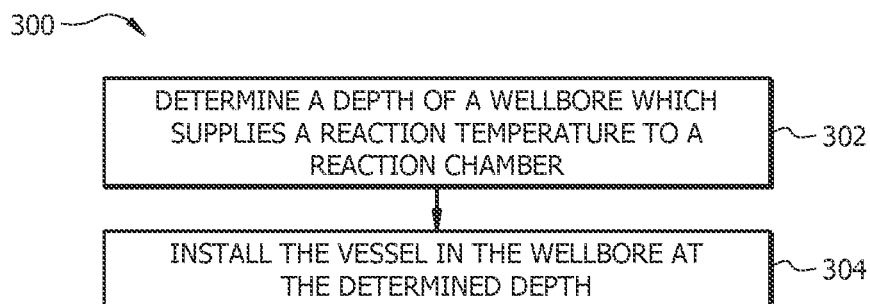
FIG. 3 is flowchart of a process for installing a vessel for use in a process for carrying out a thermochemical process according to an illustrative embodiment.

FIG. 3 is flowchart 300 of a process for installing a vessel housing a reaction chamber for use in a process for carrying out a thermochemical process according to an illustrative embodiment. Flowchart 300 begins at step 302 by determining a depth of the wellbore supplying a reaction temperature to the reaction chamber. In step 304, the vessel is installed within the wellbore at the determined depth. Once the vessel has been installed within the wellbore, then the steps of flowchart 200 can be carried out to form one or more product streams from one or more feed streams injected into the reaction chamber.

Figure 4:
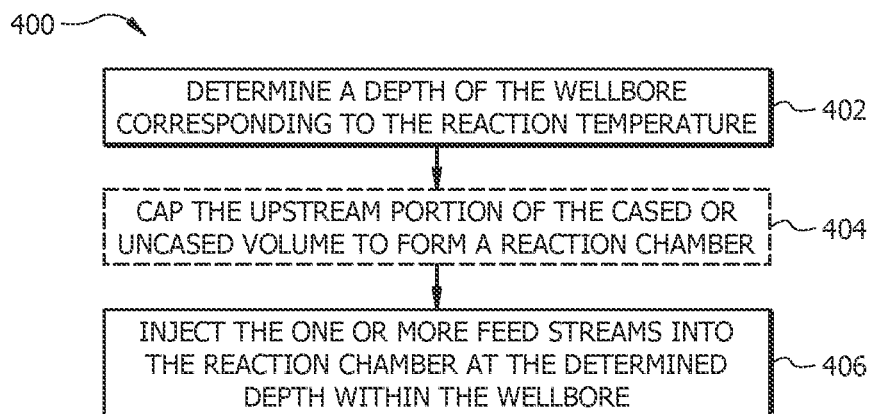
FIG. 4 is a flowchart of a more detailed process for injecting one or more feed streams into a reaction chamber according to an illustrative embodiment.

FIG. 4 is a flowchart of a more detailed process for injecting one or more feed streams into a reaction chamber according to an illustrative embodiment. The steps in flowchart 400 can be carried out in step 202 in FIG. 2 when the reaction chamber is a cased or uncased volume within the wellbore.

Flowchart 400 begins at step 402 by determining a depth of the wellbore corresponding to the reaction temperature. In an optional step 404, the upstream portion of the cased or uncased volume is capped by a casing plate to form a reaction chamber. In step 406, the one or more feed streams are injected into the reaction chamber at the determined depth within the wellbore.

Figure 5:
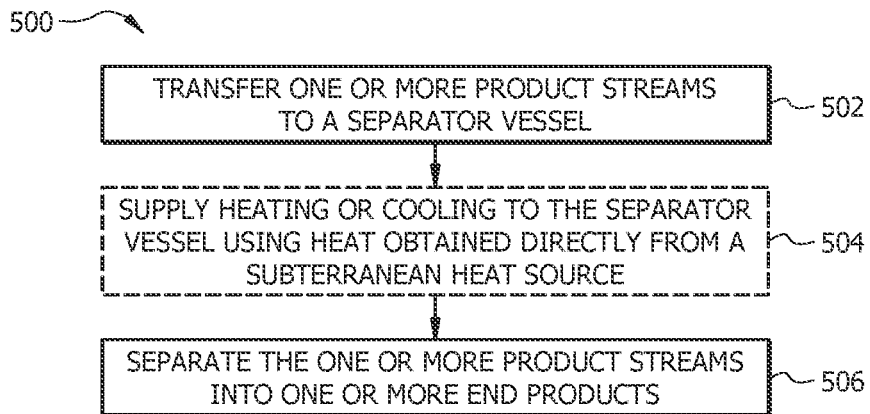
FIG. 5 is a flowchart of a process for processing a product stream formed by a thermochemical process according to an illustrative embodiment.

FIG. 5 is a flowchart of a process for processing a product stream formed by a thermochemical process according to an illustrative embodiment. Steps of flowchart 500 can be implemented following the removing step 206 in FIG. 2.

Flowchart 500 begins at step 502 by transferring the one or more product streams to a separator vessel. Depending upon the type of the separator vessel and the type of separations process implemented, the separator vessel can be heated by heating fluid that obtained its heat directly from a subterranean heat source or cooled by cooling fluid formed by heating fluid that obtained its heat directly from the subterranean heat source. Thus, flowchart 500 includes the optional step 504 of supplying heating or cooling to the separator vessel using heat obtained directly from a subterranean heat source. In step 506, the one or more product streams are separated into one or more end products.

Figure 6A:
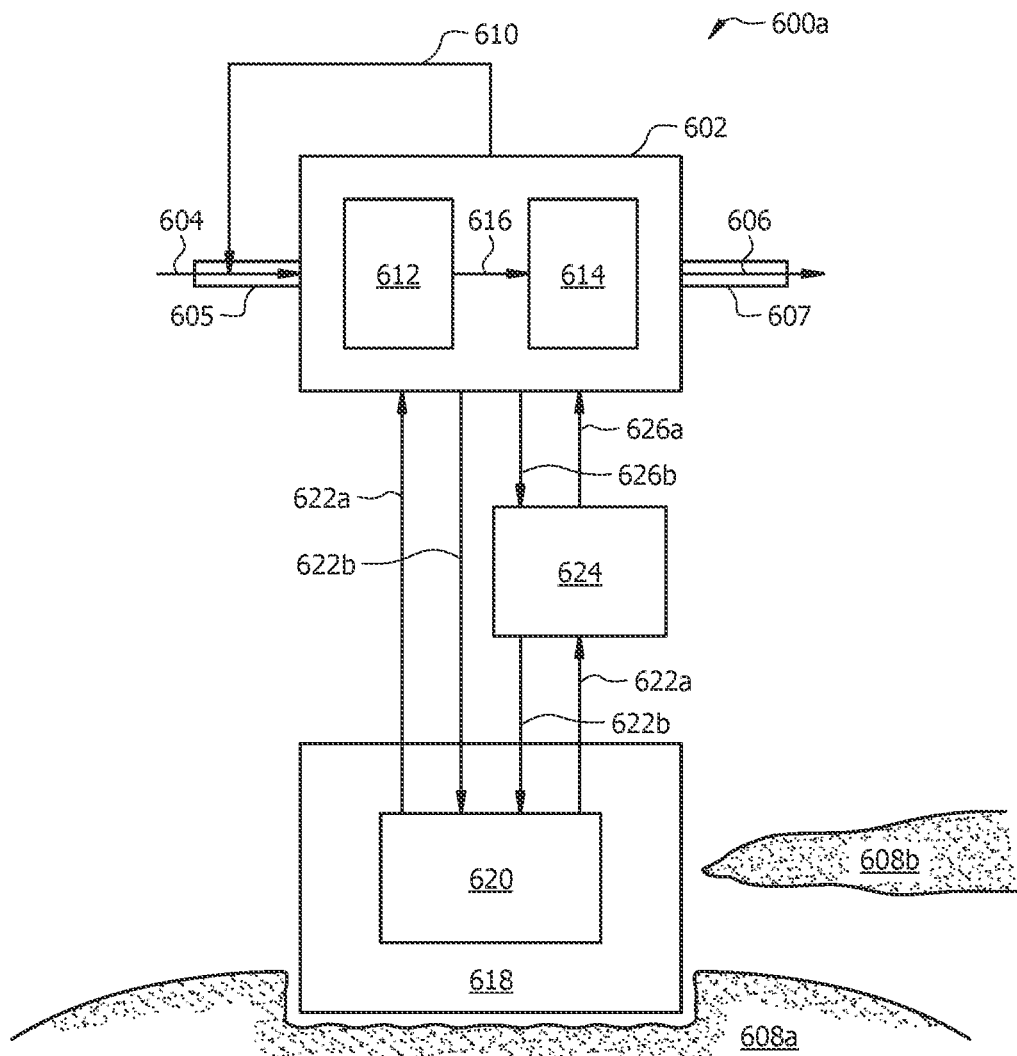
FIG. 6A is a simplified block diagram of a system for conducting thermochemical processes according to an illustrative embodiment.

FIG. 6A is a simplified block diagram of a system for carrying out a thermochemical process according to an illustrative embodiment. Non-limiting examples of thermochemical processes that can be carried out in system 600a include Haber Bosch, Fischer-Tropsch, Sabatier, and thermochemical splitting of water. Generally, system 600a includes process equipment 602 arranged to convert one or more feed streams 604 into one or more end product streams 606 by way of a thermochemical process that uses heat obtained from a subterranean heat source like magma body 608. An optional recycle stream 610 can be fed back into the one or more feed streams 604 to improve efficiency and reduce waste.

The exemplary process equipment 602 depicted in FIG. 6A includes at least a reaction chamber 612. Inlet conduit 605 facilitates input of the one or more feed streams 604 into the process equipment 602, and outlet conduit 607 facilitates flow or removal of product streams 606 from the process equipment 602. Inlet conduit 605 may include one or more valves to control the flow rate of stream 604. The reaction chamber 612 can be the interior volume of a reactor vessel. The reaction chamber 612 can be operated at higher than ambient temperatures and pressures and for conducting a thermochemical process. The thermochemical process can be a batch process or a continuous process. The reaction chamber 612 is depicted as a single chamber, but in another embodiment, the reaction chamber 612 can include two or more reaction chambers to permit two or more discrete reactions to occur. The multiple reaction chambers can be housed in a single reactor vessel or separately in multiple reactor vessels.

The process equipment 602 can also include optional recovery equipment 614, which can be used to recover one or more end product streams 606. Recovery equipment 614 can be any one or more conventionally known pieces of equipment, such as a distillation column, condenser, stripping column, extraction tower, or other forms of separator vessel. The condenser may be cooled using water including but not limited to water from an ocean, sea, lake, or river. In addition, the condenser may be driven by steam. The steam may be generated from a geothermal source. The recovery equipment may use heat from a geothermal source.

For example, a reaction carried out in reaction chamber 612 can produce an intermediate product stream 616 that includes a gaseous end product as well as unreacted reactants in gaseous form. The intermediate product stream 616 can be conveyed to the optional recovery equipment 614 to be separated into one or more end product streams 606 formed entirely from the desired end product, and one or more recycle streams 610 formed from the unreacted reactants. In another example, a reaction carried out in reaction chamber 612 can produce an intermediate product stream 616 that can be separated out into an optional recycle stream 610 and a plurality of different end product streams 606 using conventional separations techniques.

The reaction chamber 612 is heated by heat obtained directly from a subterranean heat source accessible by a wellbore 618. Wellbore 618 is formed from a borehole and associated structures (not shown), such as casing strings, drill stem, fluid conduit(s), wellhead, and control equipment. The borehole of the wellbore 618 extends from a surface to an underground location selected to be able to provide the requisite amount of heat to drive reactions within the reaction chamber 612. The reaction temperature is the temperature necessary for a desired thermochemical reaction to occur according to desired parameters. For example, the reaction temperature can be the temperature at which a desired thermochemical reaction can occur within a predetermined time period, at a selected pressure, using a particular catalyst, etc.

In some embodiments, the requisite amount of heat can be obtained simply by drilling to an adequate depth without regard to the presence of subterranean geological formations. In these embodiments, the subterranean heat source is simply the ambient heat that increases as a function of borehole depth.

In other embodiments, the subterranean heat source is a magma body 608 and the requisite amount of heat can be obtained by drilling the borehole to a particular location based on the presence or proximity of the magma body 608. Magma body 608 is one or more subterranean geological formations that houses magma. Non-limiting examples of magma body 608 can include sills, laccoliths, lopoliths, diapirs, and plutons. In the example in FIG. 6A, wellbore 618 is drilled so that the terminal end of its borehole is partially within a magma body 608a, e.g., a pluton, and so that the borehole passes past another magma body 608b, e.g., a lopolith.

A heat exchanger 620 disposed within the wellbore 618 can harness the heat from the subterranean heat source to provide the reaction chamber 612 with the reaction temperature for carrying out a thermochemical process. The heat exchanger 620 can be positioned at the terminal end of the borehole to harness heat from the magma body 608a or within the borehole at a predetermined depth proximate to magma body 608b to harness heat from the magma body 608b. The heat is transferred to a heating fluid 622a that is conveyed to the process equipment 602, e.g., reactor vessel housing the reaction chamber 612, to heat the reaction chamber 612. Spent heating fluid 622b is returned from the process equipment 602 to the heat exchanger 620 and recycled. Heat exchanger 620 may include one or more boilers that pressurize the process equipment 602 using heat from the subterranean heat source.

The heating fluid 622a,b may be any appropriate fluid for absorbing heat obtained from the magma body 608 and driving a thermochemical process as described in this disclosure. For example, the heating fluid 622a,b may include water, a brine solution, one or more refrigerants, a thermal oil (e.g., a natural or synthetic oil), a silicon-based fluid, a molten salt, a molten metal, or a nanofluid (e.g., a carrier fluid containing nanoparticles). The heating fluid 622a,b may be selected at least in part to limit the extent of corrosion of surfaces of various systems described in this disclosure. In some cases, such as to facilitate thermochemical processes requiring higher temperatures than can be achieved using steam or other typical heating fluids, a molten salt heating fluid 622a,b may be used. A molten salt is a salt that is a liquid at the high operating temperatures required for certain reactors (e.g., at temperatures between 1,600 and 2,300° F.). In some cases, an ionic liquid may be used as the heating fluid 622a,b. An ionic liquid is a salt that remains a liquid at more modest temperatures (e.g., at or near room temperature). In some cases, a nanofluid may be used as the heating fluid 622a,b. The nanofluid may be a molten salt or ionic liquid with nanoparticles, such as graphene nanoparticles, dispersed in the fluid. Nanoparticles have at least one dimension of 100 nanometers (nm) or less. The nanoparticles increase the thermal conductivity of the molten salt or ionic liquid carrier fluid. This disclosure recognizes that molten salts, ionic liquids, and nanofluids can provide improved performance as heating fluid 622a,b. For example, molten salts and/or ionic liquids may be stable at the high temperatures that can be reached through heat transfer with magma body 608. The high temperatures that can be achieved by these materials can drive thermochemical processes and/or provide other improvements to performance and/or efficiency that were previously inaccessible using conventional geothermal technology.

The subterranean heat source can also provide lower-than-ambient temperatures for the thermochemical process carried out in system 600a by implementation of an optional absorption chiller 624. The absorption chiller 624 can receive a heating fluid 622a from a heat exchanger 620 to form a cooling fluid 626a that can be conveyed to process equipment 602, e.g., to recovery equipment 614. The recovery equipment 614 can be a condenser that can condense a gaseous end product into a liquid phase for separation from unreacted reactants in the gaseous phase. Spent cooling fluid 626b can be returned to the absorption chiller 624 and reused. Spent heating fluid 622b can be returned from the absorption chiller 624 to the heat exchanger 620 and also reused.

Although not depicted in FIG. 6A, a catalyst can be provided to facilitate the thermochemical process. As discussed in more detail in the figure that follow, the catalyst can be located within the reaction chamber 612.

Figure 6B:
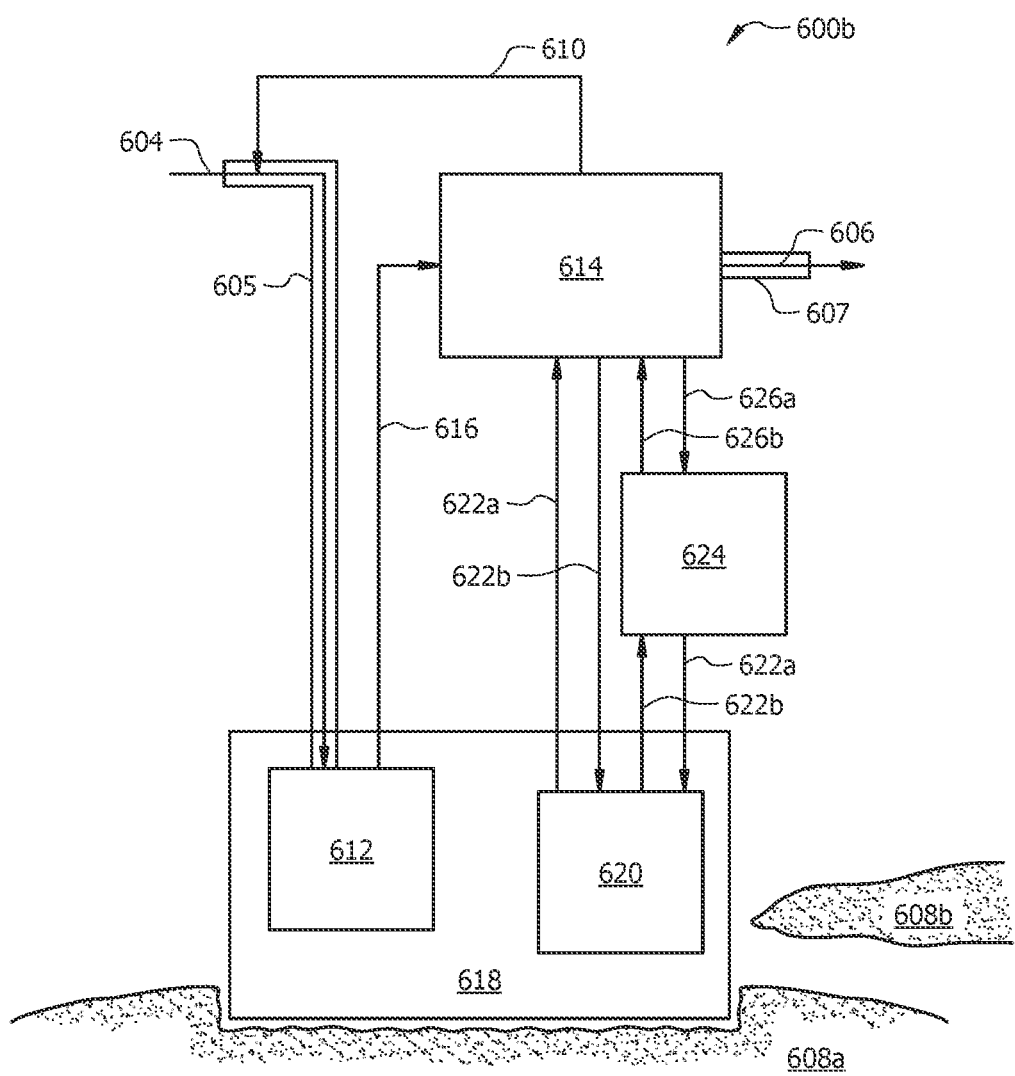
FIG. 6B is a simplified block diagram of a system for conducting thermochemical processes according to an illustrative embodiment.

FIG. 6B is a simplified block diagram of another system for conducting thermochemical processes according to an illustrative embodiment. Non-limiting examples of thermochemical processes that can be carried out in system 600b include Haber Bosch, Fischer-Tropsch, Sabatier, and thermochemical splitting of water.

Generally, system 600b includes process equipment arranged to convert one or more feed streams 604 into one or more end product streams 606 by way of a thermochemical process that uses heat obtained directly from a subterranean heat source, such as magma body 608. An optional recycle stream 610 can be fed back into the one or more feed streams 604 to improve efficiency and reduce waste.

System 600b differs from system 600a in that the reaction chamber 612 is located within the wellbore 618 to obtain heat directly from a subterranean heat source, e.g., magma body 608, rather than from a heat exchanger that harnesses the heat used by a reaction chamber located externally to the wellbore 618. In system 600b, the reaction chamber 612 can be the interior volume of a reactor vessel that is positioned within the wellbore 618.

In another embodiment, a volume within the wellbore 618 can serve as the reaction chamber 612. In this other embodiment, cased or uncased portions of the wellbore 618 can serve as the reaction chamber 612. Heat is provided to the reaction chamber 612 through the sidewalls of the wellbore 618 and through casing segments when present. The reaction chamber 612 can include additional equipment to increase the residence time of the reactants in the reaction chamber 612 or to promote exposure to a catalyst (not shown). For example, the reaction chamber can include a casing plate (not shown) that at least partially seals an upper end of the reaction chamber 612. The catalyst can be suspended from or otherwise coupled to the casing plate. In addition, or in the alternative, the reaction chamber 612 can house a baffle system (not shown) that promotes mixing and/or increases residence time of reactants in the reaction chamber 612.

Thermochemical Water Splitting

Figure 7A:
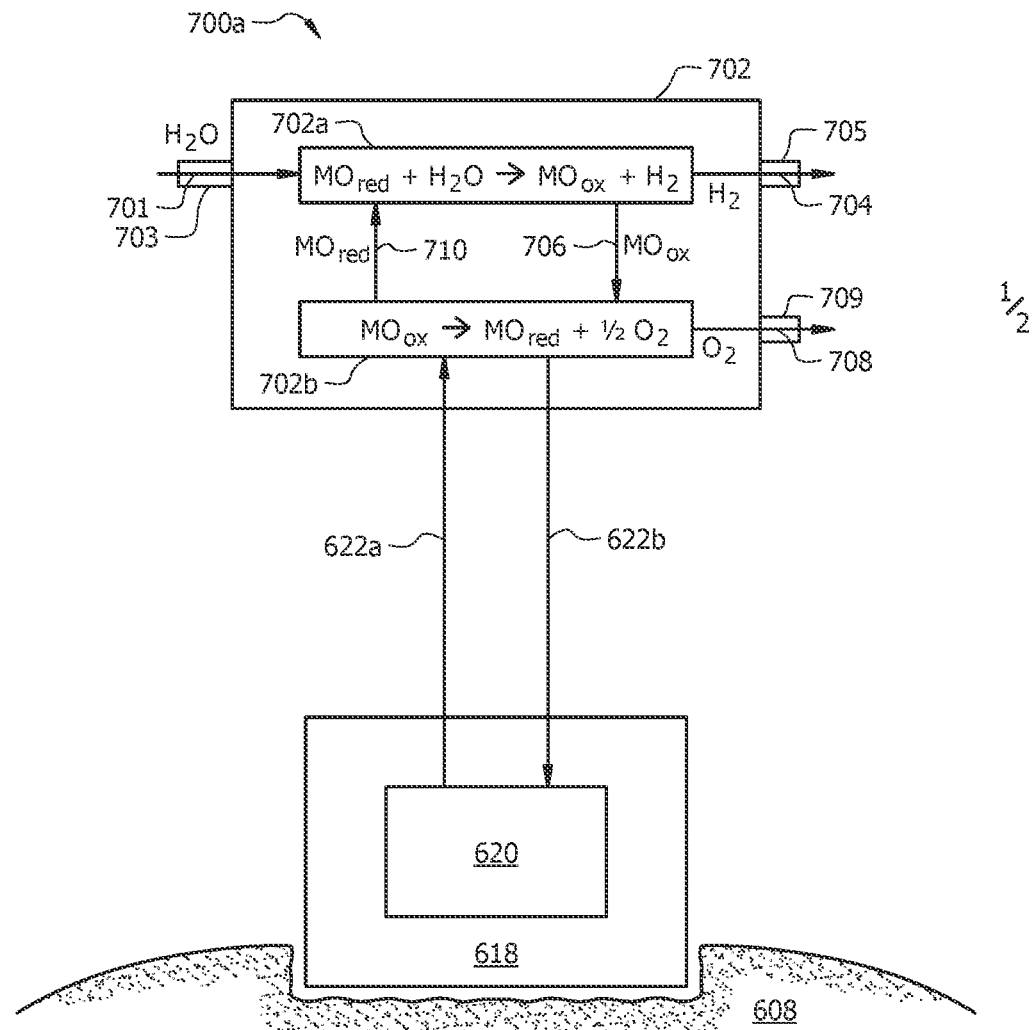
FIG. 7A is a simplified block diagram of a system for thermochemical splitting of water according to an illustrative embodiment.

FIG. 7A is a simplified block diagram of a system for thermochemical splitting of water according to an illustrative embodiment.

In thermochemical water splitting reactions, water is decomposed into hydrogen and oxygen via a series of two or more chemical reactions in which intermediate substances, referred to as catalysts, are cycled between an oxidized and reduced state and the energy needed to drive the reactions is introduced as heat. A simple two-step thermochemical water-splitting reaction to produce hydrogen generally requires very high temperature for endothermic metal oxide reduction to release oxygen and a lower temperature exothermic reaction of water with the metal, increasing the oxidation state of the metal and releasing hydrogen.

The thermochemical splitting of water can occur according to any number of conventionally available processes, but the exemplary process described in FIG. 7A is described as a metal oxide redox reaction for the sake of simplicity and consistency. General reactions for metal oxide redox reaction for the thermochemical splitting of water includes two steps:

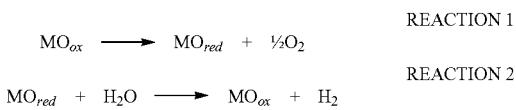

$$MO_{ox} \longrightarrow MO_{red} + \tfrac{1}{2}O_2 \quad \text{REACTION 1}$$

$$MO_{red} + H_2O \longrightarrow MO_{ox} + H_2 \quad \text{REACTION 2}$$

The first reaction represents an endothermic reaction, and the second reaction represents an exothermic reaction.

Some example classes of reactions for the thermochemical splitting of water are shown in Table 1 below.

of reactions is referred to as the Volatile Metal Oxide class (see Table 1 above). However, some metal oxides can undergo reduction and oxidation without volatilization of the metal. Reactions involving these metal oxides are referred to as Non-Volatile Metal Oxide reactions. Reactions in these two classes generally involve very high temperatures (>1400° C.). In addition to the example metal-oxide catalysts shown in Table 1, suitable catalyst may also include $ABO_3$-type perovskites such as perovskite $BiVO_3$.

The non-volatile metal oxide may include copper iron oxide nanocluster, iron-based oxides, ferrites or ferrite-supported zirconia, cerium oxide or cerium-oxide-supported zirconia. The zirconia may be monoclinic zirconia, cubic zirconia, or tetragonal zirconia. Cubic zirconia may be any of yttria, calcia, and magnesia as a stabilizer. The ferrite may be nickel ferrite or nickel-ferrite-supported mono clinic zirconia. The particle sizes of the metal oxide particles may be in a range of 200 to 750 μm. The iron-based oxide may be $NiFe_2O_4/m\text{-}ZrO_2$.

As an alternative to using metal-oxide catalysts, thermal reduction of other chemicals can be used to facilitate water splitting reactions at lower temperatures. An intermediate reaction is typically necessary to release hydrogen and another reaction (sometimes more than one) is required to restore the oxidation state of the initial compound. These lower temperature reactions generally either employ intermediates for oxidation, complicating the reaction chemistry, or use electrolysis to release hydrogen and restore the original oxidation state of the intermediate substances (catalysts). For example, the sulfuric acid process shown in Table 1 is one of very few low-temperature thermochemical cycles that operate at a moderate temperature (~850° C.). however,

TABLE 1

Example reactions

| Reaction class | Chemical Reactions | Temperature (° C.) |
|---|---|---|
| Volatile Metal Oxide | $CdO(s) \longrightarrow CdO(g) + \tfrac{1}{2}O_2(g)$ | 1450 |
|  | $Cd(l,s) + H_2O \longrightarrow CdO(s) + H_2(g)$ | 25–450 |
| Non-Volatile Metal Oxide Ferrite: | $NiMnFe_4O_8(s) \longrightarrow NiMnFe_4O_6(s) + O_2(g)$ | ~1800 |
|  | $NiMnFe_4O_6(s) + H_2O(g) \longrightarrow NiMnFe_4O_8(s) + H_2(g)$ | ~800 |
| Non-Volatile Metal Oxide | $2a\text{-}NaMnO_2(s) + H_2O(l) \longrightarrow Mn_2O_3(s) + 2NaOH(a)$ | ~100 |
|  | $Mn_2O_3(s) \longrightarrow 4MnO(s) + O_2(g)$ | ~100 |
|  | $2MnO(s) + 2NaOH \longrightarrow 2a\text{-}NaMnO_2(s) + H_2(g)$ |  |
| Sulfuric Acid | $2H_2SO_4(g) \longrightarrow 2SO_2(g) + 2H_2O(g) + O_2(g)$ | ~850 |
|  | $I_2 + SO_2(a) + 2H_2O \longrightarrow 2HI(a) + H_2SO_4(a)$ | ~100 |
|  | $2HI \longrightarrow I_2(g) + H_2(g)$ | ~300 |
| Hybrid Copper Chloride | $2CuCl_2 + H_2O \longrightarrow Cu_2OCl_2 + 2HCl$ | ~400 |
|  | $2Cu_2OCl_2 \longrightarrow O_2 + 4CuCl$ | ~500 |
|  | $2CuCl + 2HCl^{e-} \longrightarrow 2CuCl_2 + H_2$ | ~100 |

In most two-step water-splitting reactions, the temperature for reduction of a metal-oxide intermediate exceeds the vaporization temperature of the metal, such that a vapor-phase metal is created in an initial reaction step. This class this multi-step process requires an intermediate substance (catalyst) to regenerate the intermediate compound ($H_2SO_4$ in this example). The sulfuric acid reaction can be achieved through a two-step process by using an electrolytic step to regenerate the intermediate compound. Such electrolytic cycles are referred to as a Hybrid Reaction class.

The system 700a includes a reactor vessel 702 that includes a first reaction chamber 702a that accommodates an exothermic reaction of the thermochemical splitting process and a second reaction chamber 702b that accommodates an endothermic reaction of the thermochemical splitting process. While the reactor vessel 702 is depicted as a single vessel housing reaction chambers 702a and 702b, in another embodiment the reactor vessel 702 can be formed from two or more separate vessels, each housing one reaction chamber, and located in proximity to one another. Alternatively, the reactor vessel 702 can also be formed from two or more separate vessels located remote from one another, as in the embodiment in which the endothermic reaction of the thermochemical splitting process is carried out in a wellbore as described in more detail below.

Heat for the endothermic step is provided by a heat exchanger 620 positioned within a wellbore 618, which can harness heat from a subterranean heat source as previously described in FIG. 6A. In another embodiment, the second reaction chamber 702b can be located within the wellbore 618 to obviate the need for the underground heat exchanger 620. As previously described in FIG. 6B, the second reaction chamber can be housed within a reactor vessel positioned within the wellbore 618, or the second reaction chamber 702b can be formed from a cased or uncased volume within the wellbore 618 as shown in FIG. 6B.

Referring back to FIG. 7A, a water feed stream 701 is provided to the first reaction chamber 702a via inlet conduit 703 to produce an $H_2$ product stream 704 and an $MO_{ox}$ intermediate product stream 706 that is fed into the second reaction chamber 702b. The second reaction chamber 702b is heated by heat obtained directly from a subterranean heat source to produce an $O_2$ product stream 708 and an $MO_{red}$ intermediate product stream 710 that is fed back into the first reaction chamber 702a. In some embodiments, the heat provided by the subterranean heat source provides the endothermic reaction occurring in the second reaction chamber 702b with a reaction temperature of 1,500° C. or higher, which can be easily achieved when the reaction chamber 702b is located within the wellbore 618. $H_2$ product stream 704 may exit the reactor vessel 702 via fluid conduit 705, and $O_2$ product stream 708 may exit the reactor vessel 702 via fluid conduit 709. Although not shown, the $H_2$ product stream 704 can be fluidically coupled to a system for generating hydrocarbon fuels and other chemical products, such as the Fischer-Tropsch and Sabatier systems described in more detail in FIGS. 10, 11A, and 11B that follow.

In an example operation of system 700a of FIG. 7A, REACTION 1 occurs in the second reaction chamber 702b, to form an oxygen product stream 708 and a reduced intermediate product. REACTION 1 is an endothermic reaction. The heat for the reaction may be obtained from the wellbore 618. The reduced intermediate product stream 710 is fed to the first reaction chamber 702a. A water feed stream is provided to the first reaction chamber 702a. The reaction in reaction chamber 702a proceeds according to REACTION 2 above and produces a hydrogen product stream 704 and an oxidized metal oxide catalyst product stream 706 that is fed to the second reaction chamber 702b. REACTION 2 is an exothermic reaction. Final product streams 914 (oxygen) and 916 (hydrogen) are stored or sent to downstream process.

Figure 7B:
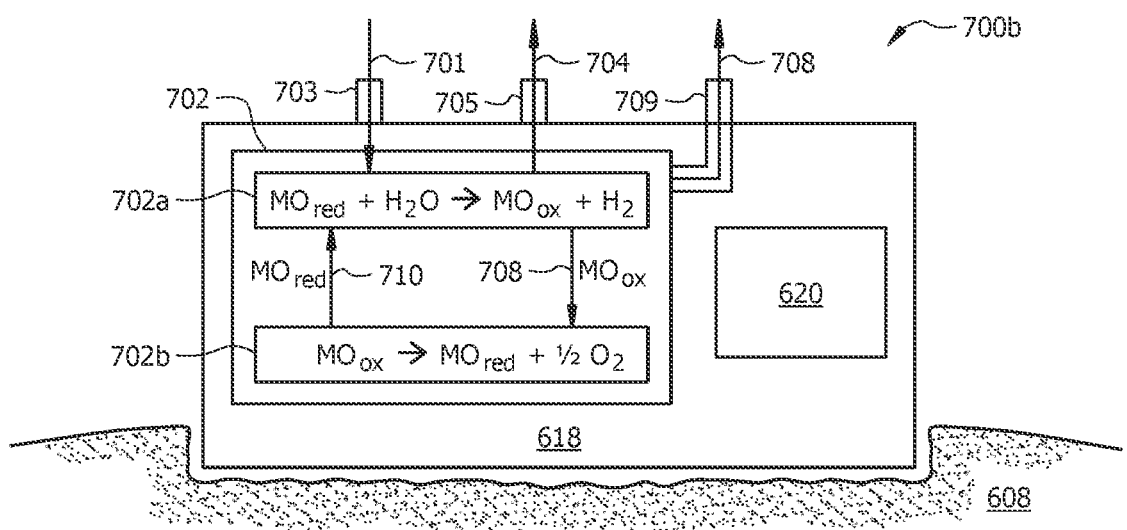
FIG. 7B is a simplified block diagram of a system for thermochemical splitting of water according to an illustrative embodiment.

In an example operation of system 700b of FIG. 7B, REACTION 1 occurs in the second reaction chamber 702b, to form an oxygen product stream 708 and a reduced intermediate product. REACTION 1 is an endothermic reaction. Endothermic reaction chamber 702b is located within a wellbore 618. The reduced intermediate product stream 710 is fed to the first reaction chamber 702a. A water feed stream is provided to the first reaction chamber 702a. The reaction in the first reaction chamber 702a proceeds according to REACTION 2 above and produces a hydrogen product stream 704 and an oxidized metal oxide catalyst product stream 706 that is fed to the second reaction chamber 702b. REACTION 2 is an exothermic reaction. Final product streams 914 (oxygen) and 916 (hydrogen) are stored or sent to a downstream process. In this example in FIG. 7B, the reaction chamber 702a is shown housed within the wellbore 618 along with the reaction chamber 702b. The reaction chamber 702a can be placed at a location or depth within the wellbore 618 that is unlikely to expose the reaction chamber 702a to elevated temperatures that could adversely affect the reaction rate of REACTION 2, which is an exothermic reaction. Because temperature within the wellbore 618 generally increases with depth, the reaction chamber 702a can be placed closer to the surface than reaction chamber 702b and/or insulated to protect against exposure to elevated temperatures within the wellbore 618. In another example, the reaction chamber 702a can be housed outside of the wellbore 618 and fluidically coupled with the reaction chamber 702b that is housed within the wellbore 618.

Iodine-Sulfur Process for Thermochemical Water Splitting

Figure 8A:
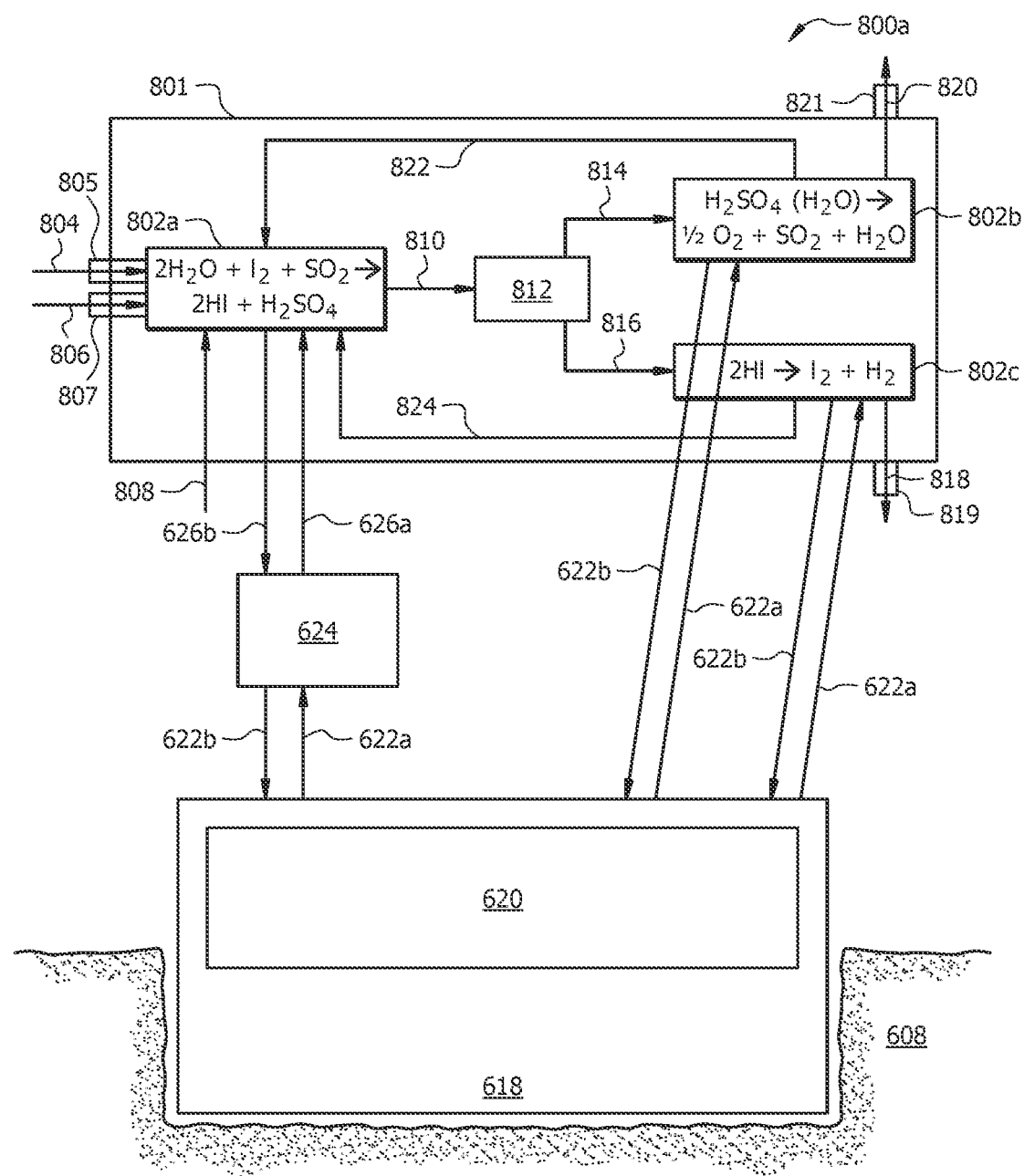
FIG. 8A is a simplified block diagram of a system for thermochemical splitting of water according to an illustrative embodiment.

FIG. 8A is a simplified block diagram of a system for thermochemical splitting of water according to an illustrative embodiment. The system 800a includes a reactor vessel 801 as well as the wellbore 618, the heat exchanger 620, and absorption chiller 624 of FIG. 6A. The reactor vessel 801 includes a first reaction chamber 802a that accommodates an exothermic reaction of the thermochemical splitting process, a second reaction chamber 802b that accommodates an endothermic reaction, and a third chamber 802c that accommodates endothermic reaction of the thermochemical splitting process. Inlet conduit 805, 807 facilitates input of feed streams 804, 806 into the reactor vessel 801, and outlet conduit 819, 821 facilitates flow or removal of product streams 818, 820 from the reactor vessel 801. Inlet conduit 805, 807 may include one or more valves to control the flow rate of streams 804, 806. The reactor vessel 801 may also include one or more separation chambers 812. In the example of FIG. 8A, the separation chamber 812 separates a product stream 810 from the first reaction chamber 802a into a first product stream 814 that is provided to the second reaction chamber 802b and a second product stream 816 that is provided to the third reaction chamber 802c. While the reactor vessel 801 is depicted as a single vessel housing reaction chambers 802a, 802b, and 802c, in another embodiment, the reactor vessel 801 can be formed from two or more separate vessels, each housing one reaction chamber, and located in proximity to one another.

Alternatively, the reactor vessel 801 can also be formed from two or more separate vessels located remote from one another, as in the embodiment in which the endothermic reaction of the thermochemical splitting process is carried out in the wellbore 618, as described in more detail below with reference to FIG. 8B. The system 800b facilitates more efficient and effective heating of reactants directly using heat from a subterranean heat source in the second reaction chamber 802b and third reaction chamber 802c to drive endothermic reactions. The subterranean heat source may be a magma body 608.

Referring back to FIG. 8A, in some embodiments, improved cooling of exothermic reactors and separation devices may be achieved using heat from the subterranean heat source. For example, the absorption chiller 624 may provide cooling with little or no energy from an electrical power grid or another energy source. The subterranean heat source can also provide lower-than-ambient temperatures for the thermochemical process carried out in system 800a by implementation of an absorption chiller 624. The absorption chiller 624 can receive a heating fluid 622a from a heat exchanger 620 to form a cooling fluid 626a that can be conveyed to vessel 802, e.g., to separation chamber 812, reaction chamber 802a, or recovery equipment. The separation chamber 812 may include recovery equipment such as a condenser that can condense a gaseous end product into a liquid phase for separation from unreacted reactants in the gaseous phase. Spent cooling fluid 626b can be returned to the absorption chiller 624 and reused. Spent heating fluid 622b can be returned from the absorption chiller 624 to the heat exchanger 620 for reuse.

As previously mentioned, the thermochemical splitting of water can occur according to a variety of processes, but the exemplary process described in FIG. 8A is a sulfur-iodine reaction for the sake of simplicity and consistency. An example sulfur-iodine reaction that can be performed for performing a water splitting process may include the following steps:

REACTION 3
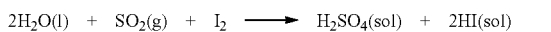

REACTION 4

REACTION 5
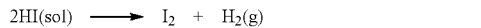

The first reaction (REACTION 3) is an exothermic reaction, which can be proceed in the first reaction chamber 802a, while the second and third reactions (REACTIONS 4 and 5) are endothermic reactions, which can proceed in the second 802b and third reaction chamber 802c respectively.

The products of REACTION 3 include a mixture of sulfuric acid and hydrogen iodide. Carrying out REACTION 3 in the presence of an excess of both sulfur dioxide and iodine, relative to the amount of water available, may result in a two-phase reaction mixture, which can be separated using liquid-liquid separation in separation chamber 812. Alternatively, sulfuric acid and hydriodic acid may be separated by gravimetric separation, because the specific gravities of sulfuric acid and hydroiodic acid are sufficiently distinct to permit gravimetric separation. After separation, sulfuric acid may be decomposed to oxygen, sulfur dioxide, and water. In one or more embodiments, the sulfuric acid may be concentrated to obtain a sulfuric acid product stream.

A water feed stream 804, a sulfur dioxide feed stream 806, an iodine feed stream 808 are provided to the first reaction chamber 802a to produce an intermediate product stream 810 comprising hydrogen iodide and sulfuric acid (see REACTION 3) that is fed into the separating chamber 812. The reaction chamber 802a may be maintained at a suitable temperature. For example, the temperature may between about 20° C. to about 120° C. The absorption chiller 624 is used to keep the reaction chamber 802a at suitable temperature. The absorption chiller 624 can receive a heating fluid 622a from a heat exchanger 620 to form a cooling fluid 626a that can be conveyed to vessel 802, e.g., to separation chamber 812, reaction chamber 802a, or recovery equipment. The recovery equipment can be a condenser that can condense a gaseous end product into a liquid phase for separation from unreacted reactants in the gaseous phase. Spent cooling fluid 626b can be returned to the absorption chiller 624 and reused. Spent heating fluid 622b can be returned from the absorption chiller 624 to the heat exchanger 620 and also reused.

The sulfur dioxide feed stream 806 may include sulfur dioxide obtained from a source of sulfur dioxide. The source of sulfur dioxide may be any technically feasible feedstock, such as elementary sulfur or hydrogen sulfide, which are converted to sulfur dioxide. Both elementary sulfur and hydrogen sulfide may be converted to sulfur dioxide by reacting with an appropriate oxidant. The oxidant is preferably oxygen. The sulfur dioxide of the sulfur dioxide feed stream 806 may be obtained as a result of sulfur combustion or as a by-product of a sulfide smelter or roaster, or a $SO_2$-enrichment step of an industrial process gas cleaning plant. More generally, any other sulfur source, which can be converted to $SO_2$, may be used to obtain the sulfur dioxide feed stream 806. The sulfide may be copper, nickel, zinc, lead, or iron sulfide.

The iodine feed stream 808 may be elemental iodine. Additionally, iodine may be recycled using recycle stream 824 from the third reaction chamber 802c to the first reaction chamber 802a. The water feed stream 804 may be provided from a municipal water supply or other source of water.

As shown in REACTIONS 3 and 5, hydrogen iodide produced can be isolated in an efficient and practical manner to render it available for decomposition to hydrogen plus iodine. More specifically, the reaction of iodine, sulfur dioxide, and water can be controlled in a manner so as to yield two liquid phases which are practicably separable from each other. From one of these phases, hydrogen iodide may be derived for use in the third reaction chamber 802c, and from the other phase, sulfuric acid may be derived for use in the second reaction chamber 802b.

The separating chamber 812 may be a liquid-liquid separation system that produces a sulfuric acid intermediate product stream 814 and a hydrogen iodide 816 intermediate product steam that are fed into a second 802b and a third reaction chamber 802c respectively. Optionally, if required, the separating chamber 812 may be heated by heat obtained directly from a subterranean heat source to improve the separation efficiency.

The second reaction chamber 802b may be a decomposition chamber that decomposes sulfuric acid to produce an oxygen product stream 820, sulfur dioxide, and water. The oxygen, sulfur dioxide, and water may be subsequently separated. The sulfur dioxide and water may be recycled back via recycle stream 822 to reaction chamber 802a. Although not shown, optionally, the second reaction chamber may be used to concentrate sulfuric acid and obtain a concentrated sulfuric acid product stream.

The hydrogen iodide intermediate product stream 816 from separating chamber 812 is fed to a third reaction chamber 802c where hydrogen iodide is pyrolyzed resulting in the formation of iodine and hydrogen. The iodine and hydrogen mixture may be subsequently condensed to generate a hydrogen product stream 818 and condensed iodine, which is recycled back to the first reaction chamber 802a. The iodine is recycled back to reaction chamber 802a via recycle stream 824.

Referring to FIG. 8A, heat for the endothermic steps (REACTIONS 4 and 5) may be provided by a heat exchanger 620 positioned within a wellbore 618, which can harness heat from a subterranean heat source, such as magma body 608 as previously described in FIG. 6A. The heat is harnessed by heating fluid 622a that is conveyed to the reaction chambers 802b and 802c and then recycled back to the heat exchanger 620 for reuse. The spent heating fluid 622b is returned to the heat exchanger 620 for reuse.

Figure 8B:
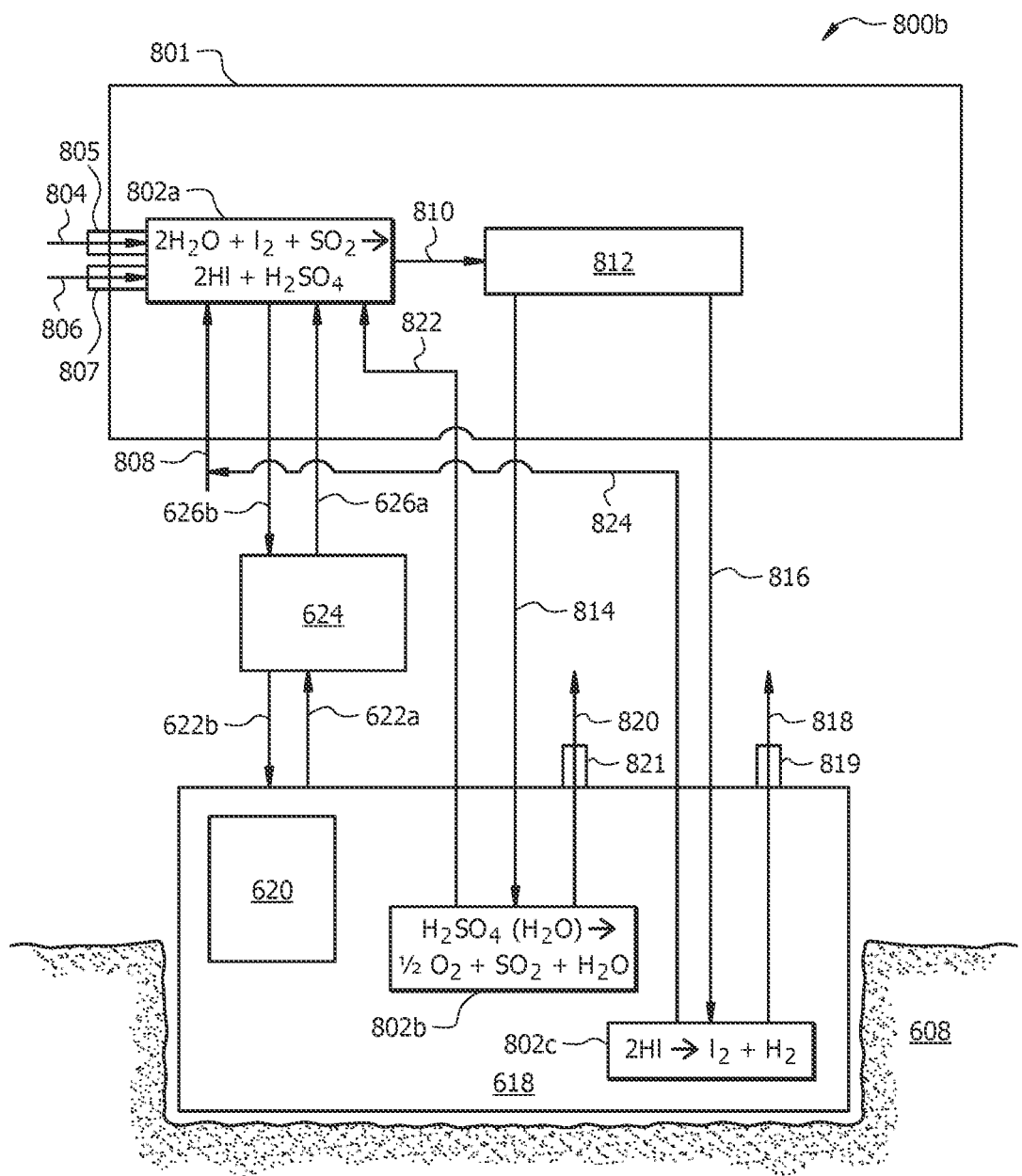
FIG. 8B is a simplified block diagram of a system for thermochemical splitting of water according to an illustrative embodiment.

In another embodiment shown in FIG. 8B, a modified reaction system 800b has the second and third reaction chambers 802b and 802c located within the wellbore 618 to obviate the need for the underground heat exchanger 620 to provide heat for the endothermic reactions. Generally, system 800b includes process equipment arranged to convert one or more feed streams 804 and 806 into one or more end product streams 818 and 820 by way of a thermochemical process that uses heat obtained directly from a subterranean heat source (e.g., magma body 608). As previously described in FIG. 6B, the second and third reaction chambers 802b and 802c can be housed within a reactor vessel positioned within the wellbore 618, or the second and third reaction chambers 802b and 802c can be formed from a cased or uncased volume within the wellbore 618. In one or more embodiments, reaction chambers 802b and 802c may be positioned at a pre-determined depth corresponding to the desired reaction temperature.

In an example operation of system 800a of FIG. 8A, feed streams 804 and 806 are provided to a first reaction chamber 802a. The reaction proceeds according to REACTION 3 above, while the chamber 802a is cooled to target temperature range using chiller 624. Intermediate product stream 810 is sent to separating chamber 812. Intermediate product streams 814 and 816 comprising sulfuric acid and hydrogen iodide are sent to endothermic reactors 802b and 802c respectively. In endothermic reactor 802b, the reaction proceeds according to REACTION 4. In endothermic reactor 802c, the reaction proceeds according to REACTION 5. Endothermic reactors are heated by heat exchanger 620. Final product streams 818 and 820 are stored or sent to downstream process. The reaction system 800a may be maintained at nonambient pressures and/or temperatures, and the resultant yields will depend on these conditions.

In an example operation of system 800b of FIG. 8B, feed streams 804 and 806 are provided to a first reaction chamber 802a. The reaction proceeds according to REACTION 3 above, while the chamber 802a is cooled to target temperature range using chiller 624. Intermediate product stream 810 is sent to separating chamber 812. Intermediate product streams 814 and 816 comprising sulfuric acid and hydrogen iodide are sent to endothermic reactors 802b and 802c respectively located within a wellbore 618. In endothermic reactor 802b, the reaction proceeds according to REACTION 4. In endothermic reactor 802c, the reaction proceeds according to REACTION 5. Endothermic reactors are heated by heat that is transferred to the wellbore 618 from the magma body 608. Final product streams 818 and 820 are stored or sent to downstream process. The reaction system 800b may be maintained at nonambient pressures and/or temperatures, and the resultant yields will depend on these conditions.

Copper-Chloride Reaction for Thermochemical Water Splitting

Figure 9A:
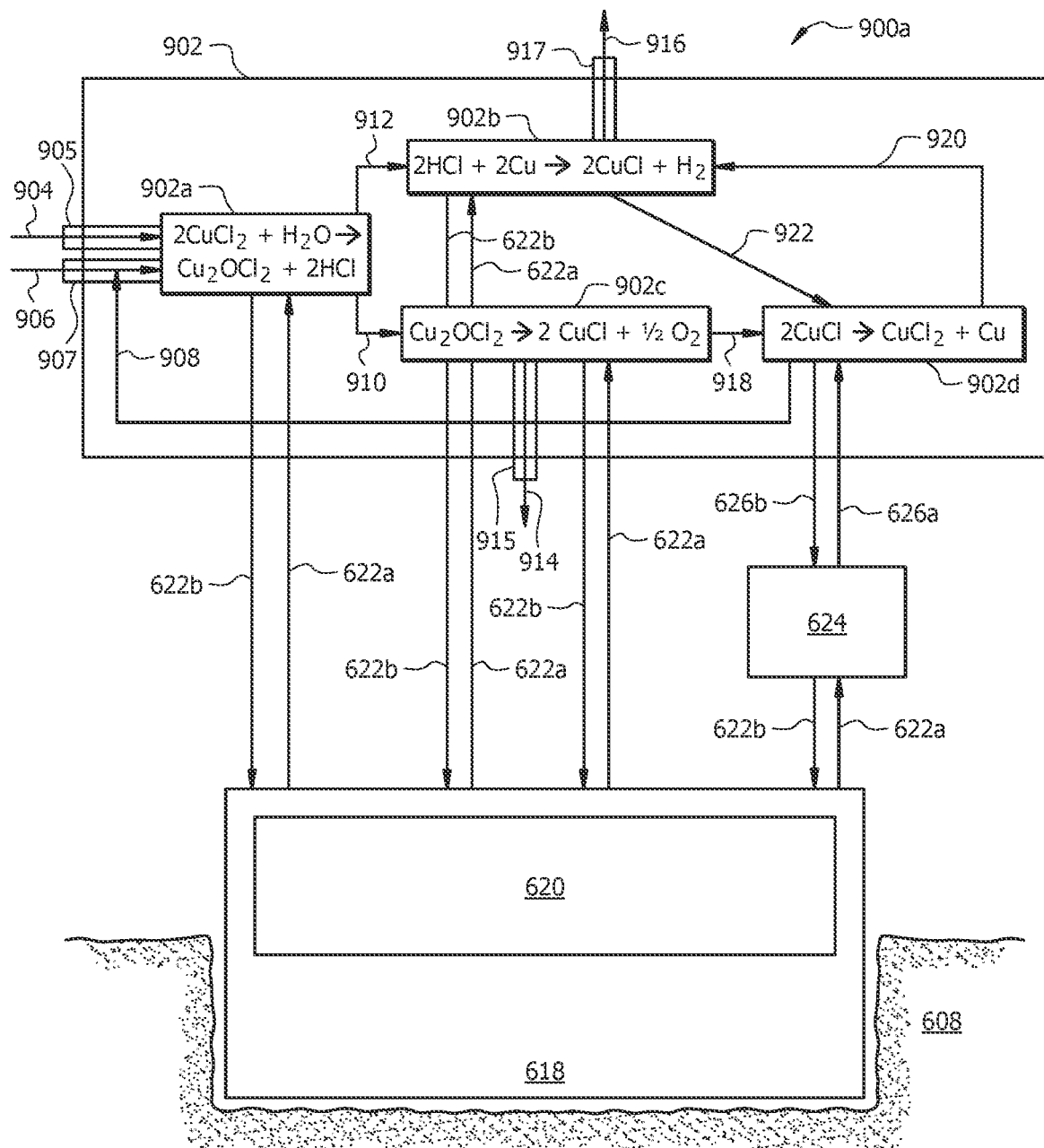
FIG. 9A is a simplified block diagram of a system for thermochemical splitting of water according to an illustrative embodiment.

FIG. 9A is a simplified block diagram of another example system 900a for thermochemical splitting of water according to an illustrative embodiment. The system 900a includes a reactor vessel 902 as well as the wellbore 618, the heat exchanger 620, and absorption chiller 624 of FIG. 6A. Inlet conduit 905, 907 facilitates input of feed streams 904, 906 into the reactor vessel 902, and outlet conduit 915, 917 facilitates flow or removal of product streams 914, 916 from the reactor vessel 902. Inlet conduit 905, 907 may include one or more valves to control the flow rate of streams 904, 906. The reactor vessel 902 includes a first reaction chamber 902a that accommodates an endothermic reaction of the thermochemical splitting process, a second reaction chamber 902b that accommodates an endothermic reaction of the thermochemical splitting process, a third chamber 902c that accommodates endothermic reaction of the thermochemical splitting process, and a fourth reaction chamber 902d that accommodates an electrochemical reaction of the thermochemical splitting process. The reactor vessel 902 may also include one or more separation chambers (not shown—see, e.g., separation chamber 812 of FIG. 8A above). While the reactor vessel 902 is depicted as a single vessel housing reaction chambers 902a, 902b, 902c, and 902d, in another embodiment, the reactor vessel 902 can be formed from two or more separate vessels, each housing one reaction chamber, and located in proximity to one another.

Alternatively, the reactor vessel 902 can also be formed from two or more separate vessels located remote from one another, as in the embodiment in which the endothermic reaction of the thermochemical splitting process is carried out in the wellbore 618, as described in more detail below with reference to FIG. 9B. The system 900b facilitates more efficient and effective heating of reactants directly using heat from a subterranean heat source in the first reaction chamber 902a, second reaction chamber 902b, and third reaction chamber 902c to drive endothermic reactions. As described above, the subterranean heat source may be a magma body 608.

Referring back to FIG. 9A, in some embodiments, improved cooling of intermediate product streams and separation devices may be achieved using heat from the subterranean heat source. For example, the absorption chiller 624 may provide cooling with little or no energy from an electrical power grid or another energy source. The subterranean heat source can also provide lower-than-ambient temperatures for the thermochemical process carried out in system 900a by implementation of an absorption chiller 624. The absorption chiller 624 can receive a heating fluid 622a from a heat exchanger 620 to form a cooling fluid 626a that can be conveyed to process vessel 902, e.g., to separation chamber (not shown) or recovery equipment. The separation chamber may include recovery equipment such as a condenser that can condense a gaseous end product into a liquid phase for separation from unreacted reactants in the gaseous phase. Spent cooling fluid 626b can be returned to the absorption chiller 624 and reused. Spent heating fluid 622b can be returned from the absorption chiller 624 to the heat exchanger 620 for reuse.

As previously mentioned, the thermochemical splitting of water can occur according to a variety of processes, but the exemplary process described in FIG. 9A is described as the copper-chlorine (Cu—Cl) process for the sake of simplicity and consistency. Thermochemical water splitting with a copper-chlorine (Cu—Cl) process is a promising process that could use heat from subterranean source to decompose water into its constituents, oxygen and hydrogen, through intermediate copper and chlorine compounds.

An example the copper-chlorine process that can be performed for performing a water splitting process may include the following steps:

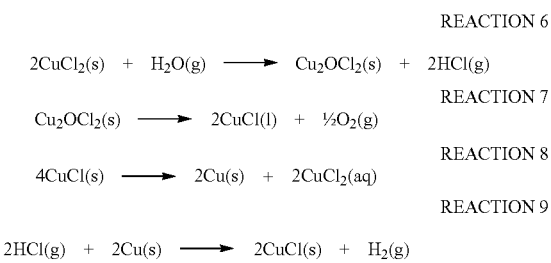

REACTION 6: $2CuCl_2(s) + H_2O(g) \longrightarrow Cu_2OCl_2(s) + 2HCl(g)$

REACTION 7: $Cu_2OCl_2(s) \longrightarrow 2CuCl(l) + \tfrac{1}{2}O_2(g)$

REACTION 8: $4CuCl(s) \longrightarrow 2Cu(s) + 2CuCl_2(aq)$

REACTION 9: $2HCl(g) + 2Cu(s) \longrightarrow 2CuCl(s) + H_2(g)$

As shown in REACTIONS 6-9, the Cu—Cl process to split water may comprise a four step process comprising the steps of 1) reacting water and solid copper chloride at a suitable temperature, preferably of about 400° C. to form solid copper chloride oxide ($Cu_2OCl_2$) and hydrogen chloride gas (REACTION 6); 2) heating $Cu_2OCl_2$ to a suitable temperature, preferably about 500° C. to about 530° C. to obtain molten copper chloride salt and oxygen gas (REACTION 7); 3) subjecting solid copper chloride to electrolysis at a suitable temperature, preferably of about 20 to about 90° C. to obtain solid copper and an aqueous slurry copper chloride (REACTION 8); and 4) reacting solid copper and hydrochloric acid gas at a suitable temperature, preferably of about 430° C. to about 475° C. to obtain solid copper chloride and hydrogen gas. The solid copper chloride may be recycled back to step 3 and subjected to the electrolysis step.

The first and second reactions (REACTION 6 and 7) are endothermic reactions, which can proceed in the first and third reaction chambers 902a and 902c, while the third reaction (REACTION 8) is an electrochemical reaction, which can proceed in the fourth reaction chamber 902d. Like the first and second reactions, the fourth reaction (REACTION 9) is an endothermic reaction, which can proceed in the second reaction chamber 902b.

A water feed stream 904 and a copper chloride feed stream 906 are provided to the first reaction chamber 902a to produce two intermediate product streams 910 and 912 comprising copper chloride oxide and hydrochloric acid respectively (see REACTION 6). The reaction chamber 902a may be provided heat from a heat exchanger 620 that obtains heat from a subterranean heat source. For example, the temperature may between about 100° C. to about 500° C.

The copper chloride feed stream 906 may include copper chloride obtained from a source of copper chloride and/or copper chloride recycled via stream 908 that may be generated during the thermochemical splitting of water.

The first reaction chamber 902a may be a fluidized bed where steam and solid copper chloride may be fed into the reactor chamber. The steam may be obtained from a geothermal well. As shown in REACTION 6, copper chloride oxide is a solid and hydrochloric acid a gas. These two intermediate products may be isolated in an efficient and practical manner.

The third reaction chamber 902c may be a decomposition chamber that decomposes copper chloride oxide to produce an oxygen product stream 914 and molten copper chloride stream 918. The second reaction chamber 902b may receive recycled copper via stream 920. Solid Cu may be fed into the second reaction chamber 902b, wherein hydrochloric acid gas from the first reaction chamber 902a reacts with the solid Cu to generate hydrogen gas product stream 916 and solid copper chloride intermediate product stream 922. The solid copper chloride intermediate product stream 922 may be fed into the fourth reaction chamber 902d.

The fourth reaction chamber 902d may be an electrolytic reactor where an electrolysis step may occur generating an aqueous solution of copper (II) chloride and solid copper at an appropriate temperature. The appropriate temperature may be maintained by implementation of an absorption chiller 624. The absorption chiller 624 can receive a heating fluid 622a from a heat exchanger 620 to form a cooling fluid 626a that can be conveyed to vessel 902, e.g., to separation chamber (not shown) or recovery equipment.

Heat for the endothermic steps (REACTIONS 6, 7 and 9) may be provided by a heat exchanger 620 positioned within a wellbore 618, which can harness heat from a subterranean heat source, such as magma body 608 as previously described in FIG. 6A. The heat is harnessed by heating fluid 622a that is conveyed to the reaction chambers 802b and 802c and then recycled back to the heat exchanger 620 for reuse. The spent heating fluid 622b is returned to the heat exchanger 620 for reuse.

Figure 9B:
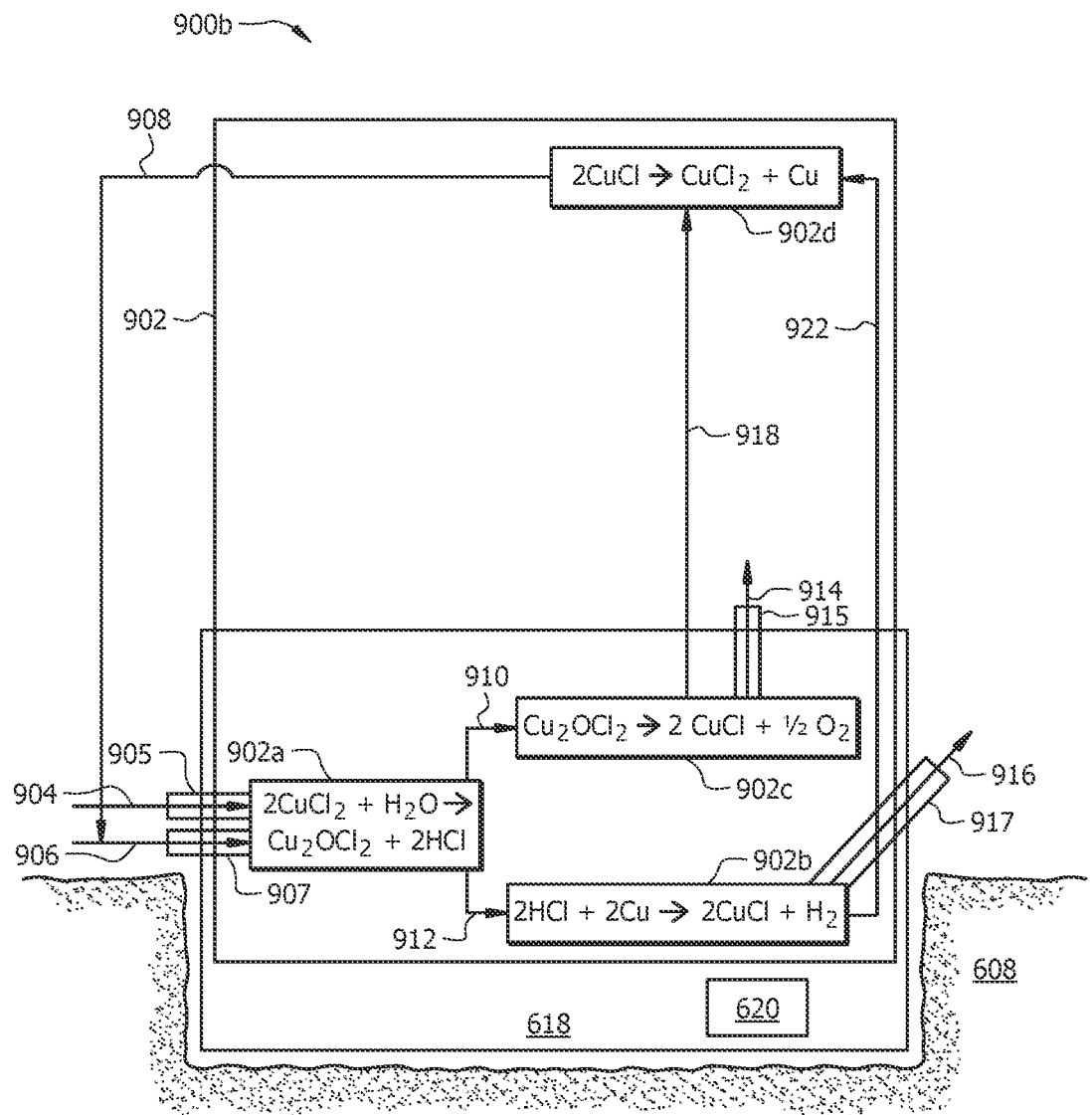
FIG. 9B is a simplified block diagram of a system for thermochemical splitting of water according to an illustrative embodiment.

In another embodiment shown in FIG. 9B, a modified reaction system 900b has the first, second, and third reaction chambers 902a, 902b and 902c located within the wellbore 618 to obviate the need for the underground heat exchanger 620 to provide heat to drive the endothermic reactions. Generally, system 900b includes process equipment arranged to convert one or more feed streams 904 and 906 into one or more end product streams 914 and 916 by way of a thermochemical process that uses heat obtained directly from a subterranean heat source, such as a magma body 608. As previously described in FIG. 6B, the first, second, and third reaction chambers 902a, 902b, and 902c can be housed within a reactor vessel positioned within the wellbore 618, or the first, second, and third reaction chambers 902a, 902b and 902c can be formed from a cased or uncased volume within the wellbore 618. In one or more embodiments, reaction chambers 902a, 902b and 902c may be positioned at a pre-determined depth corresponding to the desired reaction temperature. The reaction systems 900a and 900b may be maintained at nonambient pressures and/or temperatures, and the resultant yields will depend on these conditions.

In an example operation of system 900a of FIG. 9A, feed streams 904 and 906 are provided to a first reaction chamber 902a. The first reaction chamber is an endothermic reactor and may be a fluidized bed. The reaction proceeds according to REACTION 6 above. Intermediate solid product stream 910 (copper chloride oxide) and intermediate gas product stream 912 (hydrochloric acid) are sent to the endothermic second 902b and endothermic third 902c reactor chambers. In endothermic reactor 902b, the reaction proceeds according to REACTION 9. In endothermic reactor 902c, the reaction proceeds according to REACTION 7. Endothermic reactors are heated by heat exchanger 620. Intermediate product stream 918 (liquid copper chloride) is cooled using the absorption chiller 624 (not shown) to generate solid copper chloride that is fed into the fourth reaction chamber 902d, where an electrochemical reaction proceeds according to REACTION 8. Final product streams 914 (oxygen) and 916 (hydrogen) are stored or sent to downstream process.

In an example operation of system 900b of FIG. 9B, feed streams 904 and 906 are provided to a first reaction chamber 902a. The first reaction chamber is an endothermic reactor and may be a fluidized bed. The reaction proceeds according to REACTION 6 above. Intermediate solid product stream 910 (copper chloride oxide) and intermediate gas product stream 912 (hydrochloric acid) are sent to the endothermic second 902*b* and endothermic third 902*c* reactor chambers. In endothermic reactor 902*b*, the reaction proceeds according to REACTION 9. In endothermic reactor 902*c*, the reaction proceeds according to REACTION 7. Endothermic reaction chambers 902*a*, 902*b*, and 902*c* are located within a wellbore 618 and heated by heat transferred to the wellbore 618 from the magma body 608. Intermediate product streams 918 and/or 922 (liquid copper chloride) can be cooled using the absorption chiller 624 (not shown) to generate solid copper chloride that is fed into the fourth reaction chamber 902*d*, where an electrochemical reaction proceeds according to REACTION 8. Final product streams 914 (oxygen) and 916 (hydrogen) are stored or sent to downstream process.

Sabatier Process

Figure 10:
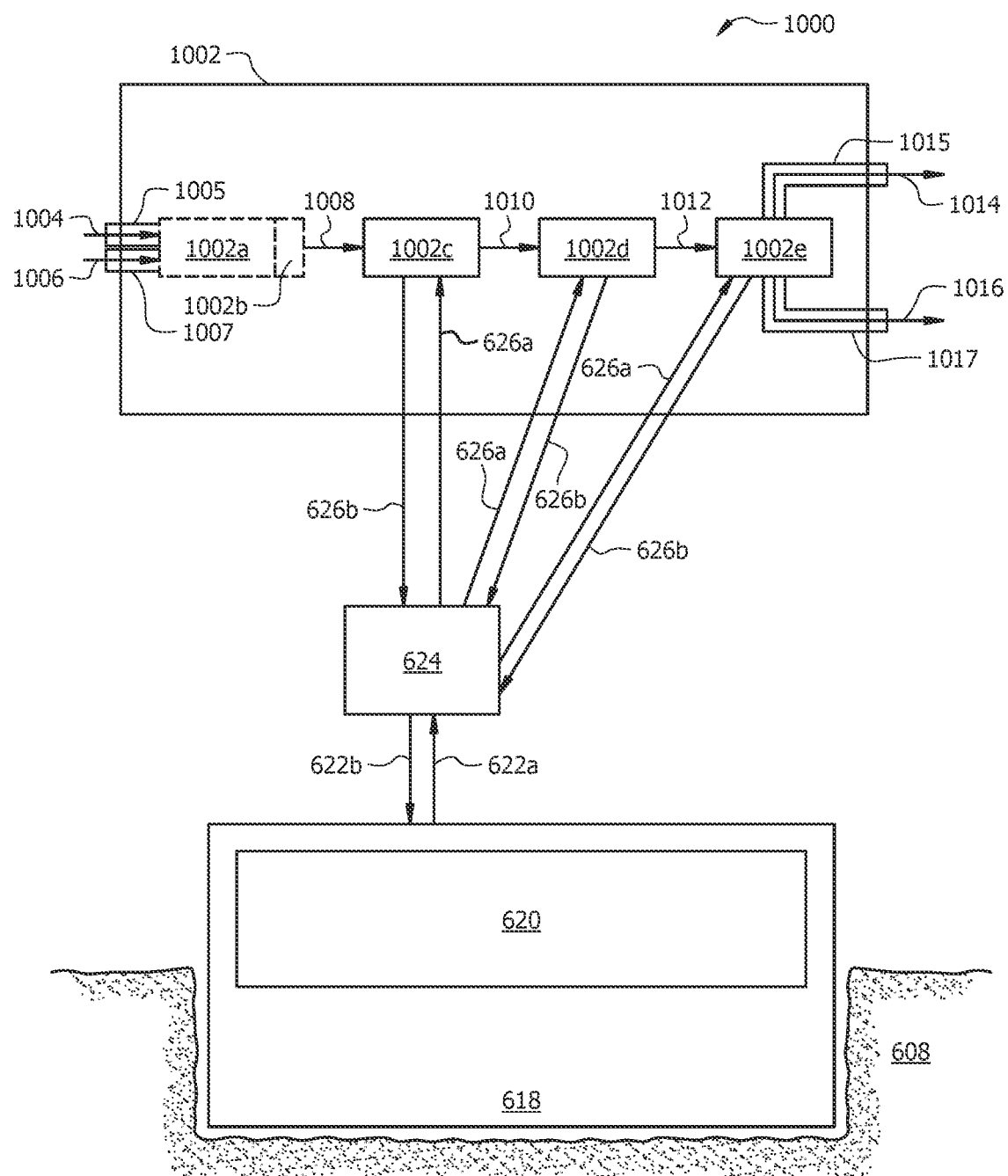
FIG. 10 is a simplified block diagram of a system for forming end products via a Sabatier process according to an illustrative embodiment.

FIG. 10 is a simplified block diagram of a system for forming end products via a Sabatier process according to an illustrative embodiment. The Sabatier reaction specifically converts a mixture of carbon dioxide and hydrogen in the presence of a catalyst into a mixture of water and methane. The system 1000 includes a reactor vessel 1002 as well as the wellbore 618, the heat exchanger 620, and absorption chiller 624 of FIG. 6A. The reactor vessel 1002 includes a reaction chamber or Sabatier reactor 1002*c* that accommodates an exothermic reaction of the Sabatier process. Inlet conduit 1005, 1007 facilitates input of feed streams 1004, 1006 into the reactor vessel 1002, and outlet conduit 1015, 1017 facilitates flow or removal of product streams 1014, 1016 from the reactor vessel 1002. Inlet conduit 1005, 1007 may include one or more valves to control the flow rate of streams 1004, 1006. The reactor vessel 1002 may also include one or more condensing heat exchangers 1002*d* and one or more separation chambers 1002*e*. The system 1000 may optionally include a carbon sorbent bed 1002*a* and a filtration device 1002*b*.

In some embodiments, improved cooling of intermediate product streams, reactors, and separation devices may be achieved using heat from the subterranean heat source. For example, the absorption chiller 624 may provide cooling with little or no energy from an electrical power grid or another energy source. The subterranean heat source can also provide lower-than-ambient temperatures for the thermochemical process carried out in system 1000 by implementation of an absorption chiller 624. The absorption chiller 624 can receive a heating fluid 622*a* from a heat exchanger 620 to form a cooling fluid 626*a* that can be conveyed to vessel 1002, e.g., to condensing heat exchangers 1002*d*, separations chamber 1002*e*, or recovery equipment. The separations chamber 1002*e* may include recovery equipment such as a condenser that can condense a gaseous end product into a liquid phase for separation from unreacted reactants in the gaseous phase. Spent cooling fluid 626*b* can be returned to the absorption chiller 624 and reused. Spent heating fluid 622*b* can be returned from the absorption chiller 624 to the heat exchanger 620 for reuse.

Referring to FIG. 10, a carbon dioxide feed 1004 and a hydrogen feed 1006 are provided to the reaction vessel 1002. The hydrogen source in the hydrogen feed stream may be hydrogen produced from the thermochemical splitting of water or any other suitable source of hydrogen.

The overall Sabatier reaction for converting carbon dioxide and hydrogen into water and methane is presented in REACTION 10. REACTIONS 11 and 12 are intermediate reaction steps in the conversion of carbon dioxide to methane. As shown in REACTION 11, hydrogen and carbon dioxide may react to form carbon monoxide and water. Next, as shown in REACTION 12, hydrogen may reduce carbon monoxide to form methane and water.

$$4H_2 + CO_2 \longrightarrow CH_4 + 2H_2O \quad \text{REACTION 10}$$

$$H_2 + CO_2 \rightleftharpoons CO + 2H_2O \quad \text{REACTION 11}$$

$$3H_2 + CO \rightleftharpoons CH_4 + H_2O \quad \text{REACTION 12}$$

One or more catalysts are used to facilitate the Sabatier reaction. Exemplary catalysts include iron, cobalt, nickel, ruthenium, rhodium, palladium, osmium, iridium, platinum, or a combination thereof, more specifically nickel, ruthenium, rhodium, or a combination thereof. The catalyst may be supported by an oxide support in any form such as a mesh, a tube, a particle bed or a combination thereof. The activity of the catalyst may be reduced by exposure to one or more contaminants. Exemplary contaminants include dimethyl sulfone ($DMSO_2$), siloxanes such as polydimethylsiloxane, organic fluorine compounds such as R-134a, and organic compounds containing chlorine such as dimethyl chloride. These contaminants may be present in very low amounts in the reactant stream to the Sabatier reactor. However, they can accumulate over time in amounts sufficient to lower the activity of the catalyst and reduce the effectiveness and efficiency of the Sabatier reactor. For example, dimethyl sulfone is a solid at room temperature (23° C.) and would not be expected to be found as a contaminant in a reactant stream of gaseous components such as carbon dioxide and hydrogen. Nonetheless dimethyl sulfone has been shown to be a primary contaminant in failed Sabatier reactors and removal of dimethyl sulfone to very low levels is desired.

As shown in FIG. 10, the reactant streams 1004 and 1006 may be optionally fed to a carbon sorbent bed 1002*a* to produce a treated reactant stream 1008 that can be introduced to the Sabatier reactor 1002*c*. The treated reactant stream 1008 may be an effective and efficient method to reduce the dimethyl sulfone concentration as well as the concentration of other contaminants in the treated reactant stream 1008 and prolong the life of the Sabatier reactor catalyst.

The carbon sorbent bed 1002*a* includes activated carbon. Activation of carbon is the process of treating the carbon to open a large number of pores in the 1 to 20 nanometer diameter range or up to 100 nanometer diameter range. Almost any carbonaceous raw material can be used for the manufacture of activated carbon. Nut shells (particularly coconut), coal, petroleum coke and other residues in either granular, briqueted or pelleted form are illustrative examples of materials which can be used. After activation the carbon has the large surface area (for example 500-1500 square meters/gram) responsible for adsorption. The activation process may include thermal decomposition in a furnace using a controlled atmosphere and heat.

The activated carbon may have a pore diameter greater than or equal to 1 nanometer (nm) or greater than or equal to 100 nm. The activated carbon may have a particle size of 4 mesh size to 40 mesh size (US mesh).

In some embodiments the carbon sorbent removes greater than or equal to 99 weight % of the dimethyl sulfone found in the reactant stream.

In some embodiments the carbon sorbent bed 1002*a* may be combined with a filtration device 1002*b*. The intermediate product stream 1008 is fed to a Sabatier reactor 1002*c*.

The design of the Sabatier reactor 1002*c* is not particularly limited and may be any of those known in the art. The Sabatier reactor 1002*c* may be a fixed-bed reactor, a fluidized-bed reactor, a microchannel reactor, a monolith reactor, or a three-phase slurry reactor. Carbon dioxide and hydrogen may react in the presence of a suitable catalyst according to REACTION 11 and REACTION 12 in the Sabatier reactor 1002*c*. Both REACTION 11 and REACTION 12 are exothermic reactions.

The absorption chiller 624 is used to keep the Sabatier reactor 1002*c* at suitable temperature. The absorption chiller 624 can receive a heating fluid 622*a* from a heat exchanger 620 to form a cooling fluid 626*a* that can be conveyed to vessel 1002, e.g., to separation chamber 1002*e*, or recovery equipment. The recovery equipment can be a condenser that can condense a gaseous end product into a liquid phase for separation from unreacted reactants in the gaseous phase. Spent cooling fluid 626*b* can be returned to the absorption chiller 624 and reused. Spent heating fluid 622*b* can be returned from the absorption chiller 624 to the heat exchanger 620 and also reused.

The separating chamber 1002*e* may be a liquid-gas separation system or gas-gas separation system that produces a methane product stream 1014 and a water or steam product stream 1016. Optionally, if required, the separating chamber 1002*e* may be heated by heat obtained directly from a subterranean heat source to improve the separation efficiency. The separating chamber 1002*e* can be a gas separator coupled with the Sabatier reactor 1002*c* to isolate methane, hydrogen, carbon dioxide, and water. It can be any device/instrument/apparatus/equipment with any technologies that are used in industry and known to those skilled in the art. It can allow some hydrogen output together with methane, a syngas mimicking natural gas. The performance of the gas separator may be important in determining the system-level efficiency.

In an example operation of system 1000 of FIG. 10, feed streams 1004 and 1006 are provided to a carbon sorbent bed 1002*a* and filtration device 1002*b* to produce a treated reactant stream 1008. The treated reactant stream 1008 is fed to a Sabatier reactor 1002*c*, where REACTIONS 11 and 12 occur. Both REACTIONS 11 and 12 are exothermic reactions. Sabatier reactor 1002*c* is cooled using the absorption chiller 624. Intermediate product stream 1010 is fed to a condensing heat exchanger 1002*d* to generate a second intermediate product stream 1012. The second intermediate product stream 1012 is fed to a gas separator 1002*e* to generate final product streams 1014 and 1016.

Fischer-Tropsch Process

Figure 11A:
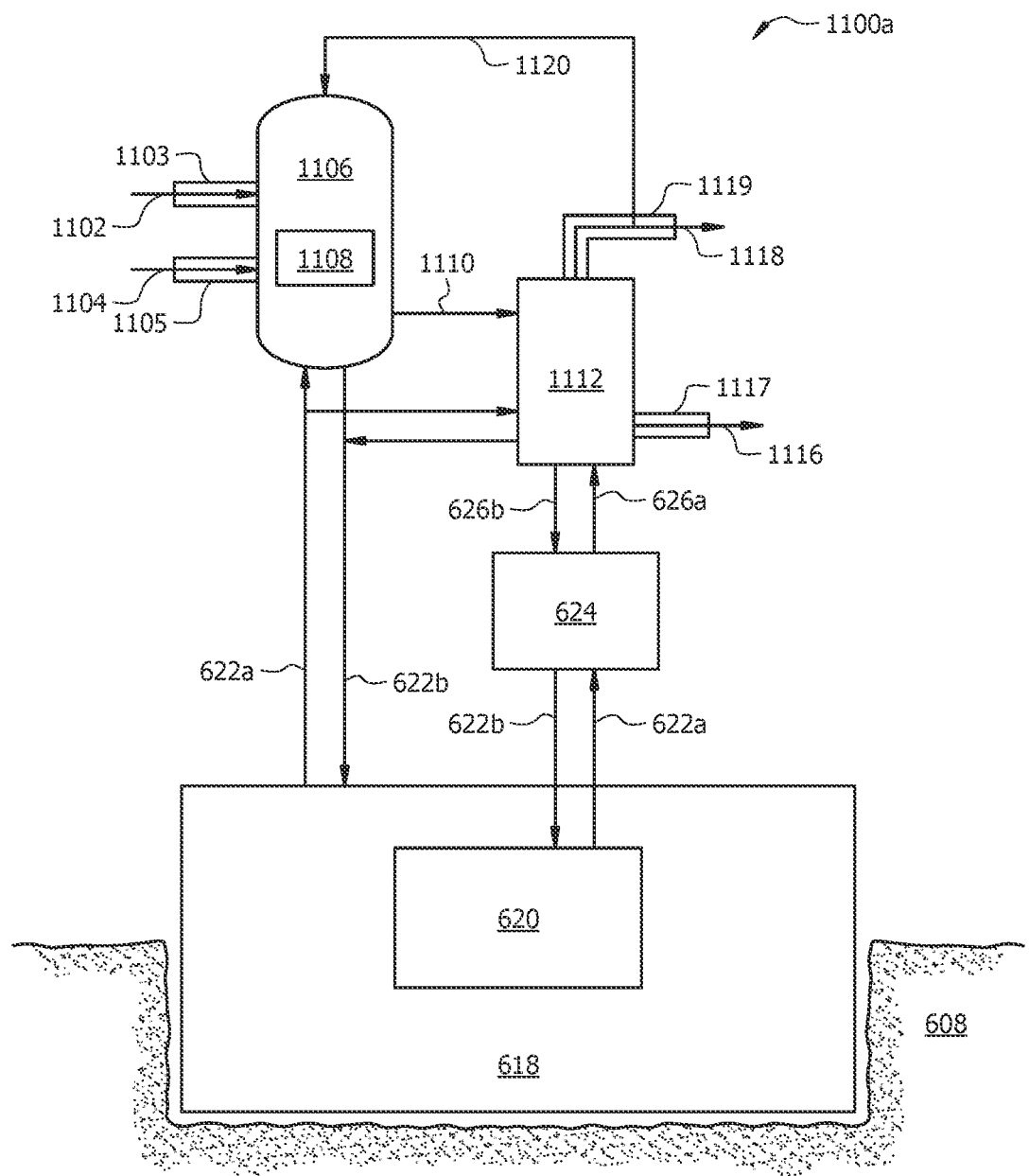
FIG. 11A is a simplified block diagram of a system for forming end products via a Fischer-Tropsch process according to an illustrative embodiment.

FIG. 11A is a simplified block diagram of a system for forming end products via a Fischer-Tropsch (FT) process according to an illustrative embodiment. The Fischer-Tropsch process is a catalytic chemical reaction that converts a synthesis gas, i.e., syngas, containing carbon monoxide (CO) and hydrogen (H2) into hydrocarbons of various molecular weights. Some of the principal FT synthesis reactions include the following:

REACTION 13
$$nCO + (2n+1)H_2 \longrightarrow C_nH_{2n+2} + nH_2O$$

REACTION 14
$$nCO + (2n)H_2 \longrightarrow C_nH_{2n} + nH_2O$$

REACTION 15
$$nCO + (2n)H_2 \longrightarrow C_nH_{2n+1} + (n-1)H_2O$$

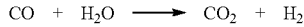
REACTION 16
$$CO + H_2O \longrightarrow CO_2 + H_2$$

System 1100*a* produces one or more liquid-phase end products 1116 and one or more gas-phase end products 1118 from a carbon monoxide feed stream 1102 via conduit 1103 and hydrogen feed stream 1104 via conduit 1105. The feed streams 1102, 1104 and, optionally, recycled products 1120 (e.g., all or a portion of end-products 1118) are supplied to a FT reactor housing a reaction chamber 1106 heated to a reaction temperature by heat obtained directly from a subterranean heat source, such as magma body 608. The FT reactor can be any conventional FT reactor, such as a multi-tubular reactor, fixed-bed reactor, an entrained flow reactor, a slurry reactor, or a circulating fluidized bed reactor.

The intermediate product stream 1110 extracted from the reaction chamber 1106 can be processed by recovery equipment 1112 to obtain the one or more liquid-phase end products 1116 and the one or more gas-phase end products 1118 using conventional processing techniques, but with heating provided by the subterranean heat source, and with cooling provided by an absorption chiller that is powered by the subterranean heat source.

In the exemplary system 1100*a*, heat is provided to the reaction chamber 1106 from a heat exchanger 620 that obtains heat directly from a subterranean heat source, such as magma body 608. The heat is harnessed by heating fluid 622*a* that is conveyed to the reaction chamber 1106 and then recycled back to the heat exchanger 620 for reuse. The heating fluid 622*a* can also be conveyed to an absorption chiller 624 that can use the heating fluid 622*a* to provide a cooling fluid 626*a* in ways that are known to those skilled in the art. The heating fluid 622*a* can also be conveyed directly to pieces of recovery equipment 1112 to facilitate processing of the intermediate stream 1110. The spent heating fluid 622*b* is returned to the heat exchanger 620 for reuse. The cooling fluid 626*a* can be used to reduce temperatures within various pieces of recovery equipment 1112 for facilitating processing of the intermediate product stream 1110 into the liquid-phase end products 1116 via conduit 1117 and the gas-phase end products 1118 via conduit 1119. Spent cooling fluid 626*b* is returned to the absorption chiller 624 for reuse.

Examples of recovery equipment 1112 can include flash drums, hydrocrackers, and separators. Variation in the process conditions, i.e., catalyst type, temperature, unit operations, molecular sieves, etc., can produce higher molecular weight hydrocarbons recovered in the liquid-phase end products 1116, such as hydrocarbon liquid fuels. The gas-phase end products 1118 can be extracted from the system 1100*a* or returned back to the FT reactor in recycle stream 1120.

Figure 11B:
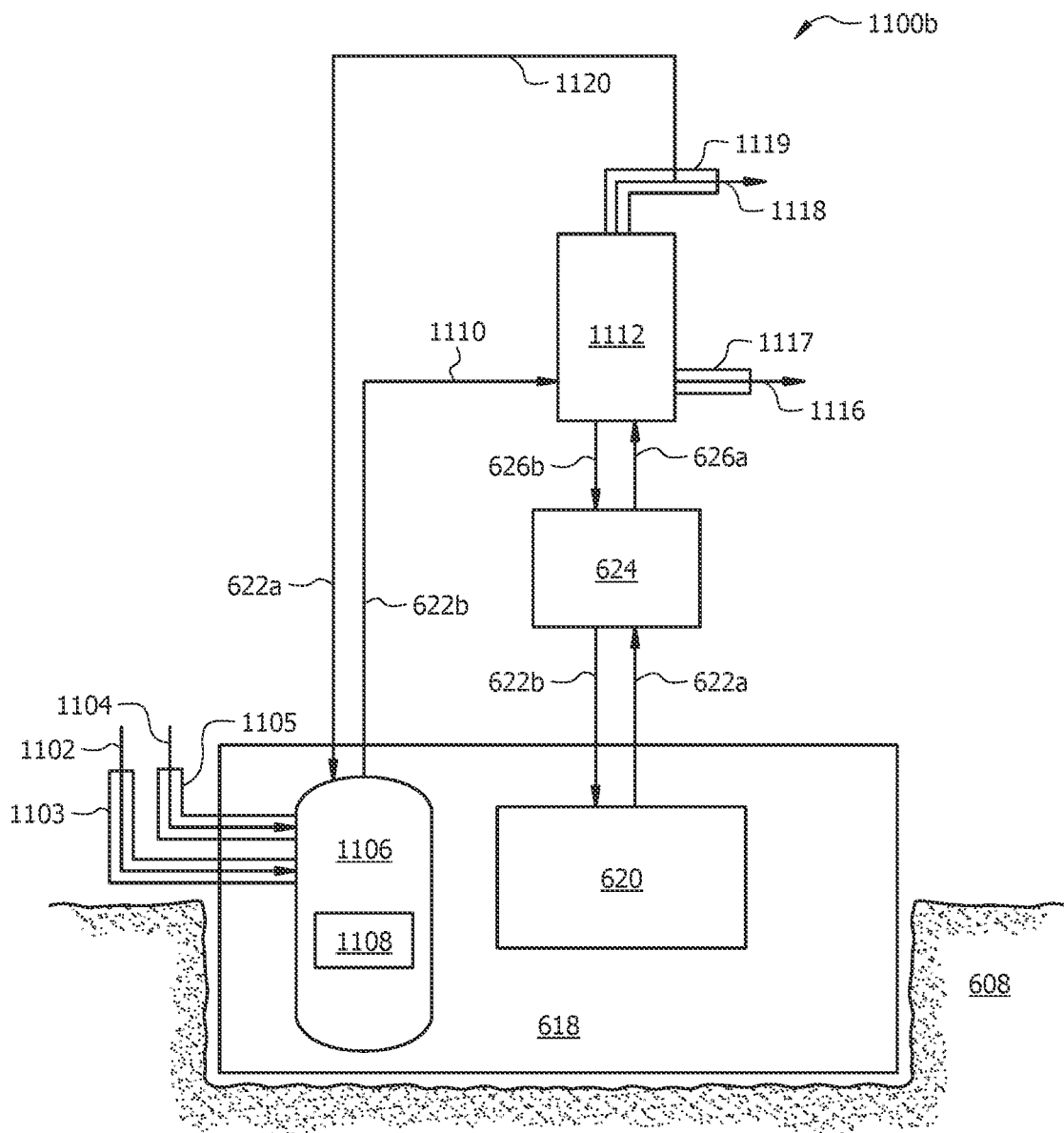
FIG. 11B is a simplified block diagram of a system for forming end products via a Fischer-Tropsch process according to an illustrative embodiment.

FIG. 11B is a simplified block diagram of another system for forming end products via a FT process according to an illustrative embodiment. The system 1100*b* is like system 1100*a* in FIG. 11A except that the FT reactor housing the reaction chamber 1108 is disposed within the wellbore 618 to obtain heat directly from the subterranean heat source, such as magma body 608. System 1100*b* can still include a heat exchanger 620 to provide heat to various pieces of recovery equipment 1112 to facilitate processing of the intermediate stream 1116, or to the absorption chiller 624 so that cooling fluid 622a can be provided to pieces of recovery equipment 1112 as previously discussed.

This disclosure describes example systems that may facilitate improved chemical processing using geothermal energy. While these example systems are described as employing heating through thermal contact with a magma reservoir (e.g., magma body 608), it should be understood that this disclosure also encompasses similar systems in which another thermal reservoir or heat source is harnessed. For example, heat transfer fluid may be heated by underground water at an elevated temperature. As another example, heat transfer fluid may be heated by radioactive material emitting thermal energy underground or at or near the surface. As yet another example, heat transfer fluid may be heated by lava, for example, in a lava lake or other formation. As such, the magma reservoir or body 608 of FIGS. 6A, 6B, 7A, 7B, 8A, 8B, 9A, 9B, 10, 11A, and 11B may be any thermal reservoir or heat source that is capable of heating heat transfer fluid to achieve desired properties (e.g., of temperature and pressure). Furthermore, the thermal reservoir or heat source may be naturally occurring or artificially created (e.g., by introducing heat underground that can be harnessed at a later time for energy generation or other thermal processes).

Additional Embodiments

The following descriptive embodiments are offered in further support of the one or more aspects of the disclosure:
1. A method for producing hydrogen by thermochemical splitting of water, the method comprising:
injecting one or more feed streams comprising water into a reaction chamber;
using heat from a subterranean heat source to form hydrogen and oxygen in the reaction chamber by one or more thermochemical reactions; and
removing, from the reaction chamber, a first product stream comprising the formed hydrogen and a second product stream comprising the formed oxygen.
2. The method of embodiment 1, wherein the subterranean heat source is a magma reservoir.
3. The method of embodiment 1, wherein the reaction chamber comprises a circulating fluidized bed of one or more non-volatile metal oxide catalysts.
4. The method of embodiment 1, further comprising increasing pressure inside the reaction chamber to generate a pressurized reaction chamber using one or more high pressure boilers, wherein the one or more high pressure boilers use the heat from the subterranean heat source.
5. The method of embodiment 4, further comprising maintaining the pressurized reaction chamber at a temperature less than 500° C. using the heat from the subterranean heat source.
6. The method of embodiment 1, further comprising recycling unreacted water back into the reaction chamber.
7. The method of embodiment 1, wherein the reaction chamber comprises a volatile metal oxide catalyst.
8. The method of embodiment 7, wherein the volatile metal oxide catalyst comprises zinc oxide or cadmium oxide.
9. The method of embodiment 1, further comprising injecting a plurality of reactant feed streams.
10. The method of embodiment 9, wherein the plurality of feed streams comprises an iodine feed stream and a sulfur dioxide feed stream.
11. The method of embodiment 9, wherein the plurality of feed streams comprises a copper feed stream and a hydrochloric acid feed stream.
12. The method of embodiment 4, wherein the pressurized reaction chamber is housed within a vessel disposed within a wellbore.
13. The method of embodiment 12, further comprising:
determining a depth of the wellbore supplying a predetermined reaction temperature to the pressurized reaction chamber; and
installing the vessel within the wellbore at the determined depth.
14. The method of embodiment 1, wherein the subterranean heat source is a magma reservoir, and wherein the reaction chamber is located at least partially within the magma reservoir.
15. The method of embodiment 1, wherein the reaction chamber is a cased or uncased volume within a wellbore.
16. The method of embodiment 12, further comprising:
determining a depth of the wellbore corresponding to a predetermined reaction temperature; and
injecting the one or more feed streams into the reaction chamber at the determined depth within the wellbore.
17. The method of embodiment 1, wherein the reaction chamber is located externally to a wellbore, and wherein the heat is supplied to the reaction chamber from a heat exchanger disposed at a depth within the wellbore to supply heating fluid to heat the reaction chamber to a predetermined reaction temperature.
18. The method of embodiment 1, further comprising:
transferring at least one of the first product stream or the second product stream to a separator vessel; and
separating the at least one of the first product stream or the second product stream into one or more end products.
19. The method of embodiment 18, further comprising:
supplying at least some of the heat to an absorption chiller to form a cooling fluid; and
cooling the separator vessel with the cooling fluid to form the one or more end products.
20. A reaction system for producing hydrogen by thermochemical splitting of water, the reaction system comprising:
a wellbore extending from a surface into a subterranean heat source;
a reaction chamber configured to be maintained at a reaction temperature using heat obtained from the subterranean heat source;
one or more inlet conduits configured to provide one or more feed streams to the reaction chamber, wherein at least one of the one or more feed streams comprise water; and
one or more outlet conduits configured to allow flow of a first product stream comprising hydrogen and a second product stream comprising oxygen.
21. The reaction system of embodiment 20, wherein the subterranean heat source is a magma reservoir.
22. The reaction system of embodiment 20, further comprising one or more high pressure boilers.
23. The reaction system of embodiment 20, further comprising one or more heat exchangers.
24. The reaction system of embodiment 20, further comprising a return conduit to recycle unreacted water back to the reaction chamber.

25. The reaction system of embodiment 20, further comprising one or more valves in one or more the inlet conduits to control the flow of the one or more of the feed streams.

26. The reaction system of embodiment 20, further comprising one or more non-volatile metal oxide catalysts disposed in the reaction chamber, wherein the one or more non-volatile metal oxide catalysts are configured to convert at least a portion of the water from the at least one of the one or more feed streams into hydrogen and oxygen in response to maintaining the water within the reaction chamber for a residence time.

27. The reaction system of embodiment 20, wherein the reaction chamber is at a surface and is heated by the heat transferred to the wellbore from the subterranean heat source.

28. The reaction system of embodiment 27, wherein the heat from the wellbore is provided to the reaction chamber by a heat transfer fluid from one or more heat exchangers in the wellbore.

29. The reaction system of embodiment 28, wherein the heat transfer fluid comprises superheated steam.

30. The reaction system of embodiment 29, wherein a spent heating fluid formed from a transfer of the heat from the heating fluid to the reaction chamber is recycled back to the one or more heat exchangers.

31. The reaction system of embodiment 20, wherein the reaction chamber is located within the wellbore.

32. The reaction system of embodiment 20, wherein the subterranean heat source is a magma reservoir, and wherein the reaction chamber extends at least partially into the magma reservoir.

33. A method for producing hydrocarbons, the method comprising:
injecting a first feed stream and a second feed stream into a reaction chamber to produce an intermediate product stream, wherein:
  the first feed stream comprises one or more oxides of carbon,
  the second feed stream comprises hydrogen, water, or both,
  the reaction chamber comprises a catalyst,
  the reaction chamber is at a temperature and a pressure, and
  the intermediate product stream comprises water, one or more hydrocarbon products, unreacted oxides of carbon and hydrogen; and
injecting the intermediate product stream from the reaction chamber into a recovery equipment to obtain one or more liquid hydrocarbon end products and one or more gas hydrocarbon end products, unreacted carbon dioxide, carbon monoxide, and hydrogen, wherein the one or more liquid hydrocarbon end products and the one or more gas hydrocarbon end products are obtained using heat from a subterranean heat source.

34. The method of embodiment 33, further comprising maintaining the temperature and pressure of the reaction chamber and recovery equipment using the heat from the subterranean heat source.

35. The method of embodiment 33, wherein the subterranean heat source is a magma reservoir.

36. The method of embodiment 35, wherein the second feed stream comprising hydrogen is obtained from a thermochemical splitting of water using heat from the subterranean heat source.

37. The method of embodiment 33, wherein:
the first feed stream comprises carbon dioxide,
the second feed stream comprises hydrogen,
the first product stream comprises methane and carbon monoxide, and
the second product stream comprises water.

38. The method of embodiment 37, wherein the catalyst comprises nickel, ruthenium, or alumina.

39. The method of embodiment 37, wherein the water is injected into a reactor that splits water into oxygen and hydrogen.

40. The method of embodiment 33, wherein:
the first feed stream comprises carbon monoxide,
the second feed stream comprises hydrogen or water,
the first product stream comprises liquid hydrocarbons, and
the second product stream comprises water.

41. The method of embodiment 33, wherein the reaction chamber is housed within a vessel disposed within a wellbore.

42. The method of embodiment 33, further comprising:
determining a depth of a wellbore supplying the reaction temperature to the reaction chamber; and
installing the reaction chamber within the wellbore at the determined depth.

43. The method of embodiment 33, wherein the reaction chamber is located at least partially within a magma reservoir.

44. The method of embodiment 33, wherein the reaction chamber is a cased or uncased volume within a wellbore.

45. The method of embodiment 33, further comprising:
determining a depth of a wellbore corresponding to the reaction temperature; and
injecting the first feed stream and the second feed stream into the reaction chamber at the determined depth within the wellbore.

46. The method of embodiment 33, wherein the reaction chamber is located externally to a wellbore, and wherein the heat is supplied to the reaction chamber by a heating fluid from a heat exchanger disposed at a depth within the wellbore, wherein the heat supplied by the heating fluid heats the reaction chamber to a predetermined reaction temperature.

47. The method of embodiment 33, wherein injecting the intermediate product stream into the recovery equipment further comprises:
transferring the intermediate product stream to a separator vessel; and
separating the intermediate product stream into the one or more liquid hydrocarbon end products and the one or more gas hydrocarbon end products.

48. The method of embodiment 47, further comprising:
supplying at least some of the heat to an absorption chiller to form a cooling fluid; and
cooling the separator vessel with the cooling fluid form the one or more liquid hydrocarbon end products and the one or more gas hydrocarbon end products.

49. A reaction system for producing hydrocarbons, the reaction system comprising:
a wellbore extending from a surface into a subterranean heat source;
a reaction chamber configured to be maintained at a reaction temperature using heat obtained from the subterranean heat source;
one or more inlet conduits configured to provide one or more feed streams to the reaction chamber, wherein at least one of the one or more feed streams comprises one or more oxides of carbon, hydrogen, or water; and outlet conduits configured to allow flow of a first product stream comprising one or more liquid hydrocarbon end products and a second product stream comprising one or more gas hydrocarbon end products.

50. The reaction system of embodiment 49, wherein the subterranean heat source is a magma reservoir.
51. The reaction system of embodiment 49, further comprising one or more high pressure boilers.
52. The reaction system of embodiment 49, further comprising one or more heat exchangers.
53. The reaction system of embodiment 49, further comprising a return conduit to recycle unreacted water back to the reaction chamber.
54. The reaction system of embodiment 49, further comprising one or more valves in one or more the inlet conduits to control the flow of the one or more of the feed streams.
55. The reaction system of embodiment 49, further comprising one or more non-volatile metal oxide catalysts disposed in the reaction chamber, wherein the one or more non-volatile metal oxide catalysts are configured to convert at least a portion of the water from the at least one of the one or more feed streams into hydrogen and oxygen in response to maintaining the water within the reaction chamber for a residence time.
56. The reaction system of embodiment 49, wherein the reaction chamber is at a surface and is heated by the heat transferred to the wellbore from the subterranean heat source.
57. The reaction system of embodiment 56, wherein the heat from the wellbore is provided to the reaction chamber by a heat transfer fluid from one or more heat exchangers in the wellbore.
58. The reaction system of embodiment 57, wherein the heat transfer fluid comprises superheated steam.
59. The reaction system of embodiment 58, wherein a spent heating fluid formed from a transfer of heat from the heating fluid to the reaction chamber is recycled back to the one or more heat exchangers.
60. The reaction system of embodiment 49, wherein the reaction chamber is located within the wellbore.
61. The reaction system of embodiment 49, wherein the subterranean heat source is a magma reservoir, and wherein the reaction chamber extends at least partially into the magma reservoir.

Although embodiments of the disclosure have been described with reference to several elements, any element described in the embodiments described herein are exemplary and can be omitted, substituted, added, combined, or rearranged as applicable to form new embodiments. A skilled person, upon reading the present specification, would recognize that such additional embodiments are effectively disclosed herein. For example, where this disclosure describes characteristics, structure, size, shape, arrangement, or composition for an element or process for making or using an element or combination of elements, the characteristics, structure, size, shape, arrangement, or composition can also be incorporated into any other element or combination of elements, or process for making or using an element or combination of elements described herein to provide additional embodiments. Moreover, items shown or discussed as coupled or directly coupled or communicating with each other may be indirectly coupled or communicating through some interface device, or intermediate component whether electrically, mechanically, fluidically, or otherwise.

While this disclosure has been particularly shown and described with reference to preferred or example embodiments, it will be understood by those skilled in the art that various changes in form and detail may be made therein without departing from the spirit and scope of the disclosure. Accordingly, this disclosure includes all modifications and equivalents of the subject matter recited in the claims appended hereto as permitted by applicable law. Changes, substitutions and alterations are ascertainable by one skilled in the art and could be made without departing from the spirit and scope disclosed herein. Moreover, any combination of the above-described elements in all possible variations thereof is encompassed by the disclosure unless otherwise indicated herein or otherwise clearly contradicted by context.

Additionally, where an embodiment is described herein as comprising some element or group of elements, additional embodiments can consist essentially of or consist of the element or group of elements. Also, although the open-ended term "comprises" is generally used herein, additional embodiments can be formed by substituting the terms "consisting essentially of" or "consisting of."

What is claimed is:

1. A reaction system for producing hydrocarbons, the reaction system comprising:
    a wellbore extending from a surface into a subterranean heat source, wherein the subterranean heat source is a magma reservoir;
    a reaction chamber configured to be maintained at a reaction temperature using heat obtained from the subterranean heat source, wherein the reaction chamber extends at least partially into the magma reservoir;
    one or more inlet conduits configured to provide one or more feed streams to the reaction chamber, wherein at least one of the one or more feed streams comprises one or more oxides of carbon, hydrogen, or water; and
    outlet conduits configured to allow flow of a first product stream comprising one or more liquid hydrocarbon end products and a second product stream comprising one or more gas hydrocarbon end products.
2. The reaction system of claim 1, further comprising one or more high pressure boilers.
3. The reaction system of claim 1, further comprising one or more heat exchangers.
4. The reaction system of claim 1, further comprising a return conduit to recycle unreacted water back to the reaction chamber.
5. The reaction system of claim 1, further comprising one or more valves in one or more the inlet conduits to control the flow of the one or more of the feed streams.
6. The reaction system of claim 1, further comprising one or more non-volatile metal oxide catalysts disposed in the reaction chamber, wherein the one or more non-volatile metal oxide catalysts are configured to convert at least a portion of the water from the at least one of the one or more feed streams into hydrogen and oxygen in response to maintaining the water within the reaction chamber for a residence time.
7. The reaction system of claim 1, wherein the reaction chamber is located within the wellbore.

* * * * *